United States Patent
Shibuya (12)

(10) Patent No.: US 7,877,336 B2
(45) Date of Patent: Jan. 25, 2011

(54) NUCLEOTIDE SEQUENCE SCREENING

(75) Inventor: Tetsuo Shibuya, Kanagawa-ken (JP)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 12/541,306

(22) Filed: Aug. 14, 2009

(65) Prior Publication Data

US 2010/0057370 A1    Mar. 4, 2010

Related U.S. Application Data

(62) Division of application No. 10/783,807, filed on Feb. 20, 2004, now Pat. No. 7,702,595.

(30) Foreign Application Priority Data

Feb. 27, 2003    (JP) .............................. 2003-050916

(51) Int. Cl.
*G06N 3/12*    (2006.01)
(52) U.S. Cl. ...................... 706/13; 702/20; 702/181; 703/2; 703/11; 211/41.12
(58) Field of Classification Search ....................... None
See application file for complete search history.

(56) References Cited

U.S. PATENT DOCUMENTS 5,706,498 A * 1/1998 Fujimiya et al. ................ 707/6
6,714,874 B1 * 3/2004 Myers et al. ................... 702/20

OTHER PUBLICATIONS

S.F. Altschul et al., "Basic Local Alignment Search Tool," J. Mol. Biol. vol. 215, No. 3, pp. 403-410, 1990.
W.R. Pearson et al., "Improved Tools for Biological Sequence Comparison," Proc. Natl. Acad. Sci., vol. 85, No. 8, pp. 2444-2448, Apr. 1988.
T.F. Smith et al., "Identification of Common Molecular Subsequences," J. Mol. Biol., vol. 147, pp. 195-197, 1981.
T. Arakawa et al., "Development of Novel cDNA Array System," The Issue Culture Engineering, vol. 27, No. 2, pp. 76-79, Feb. 2001.
T. Shibuya et al., "Accurate cDNA Clustering Algorithm Based on Spliced Sequence Alignment," Technical Report of IEICE, vol. 102, No. 90, pp. 17-24, May 2002.
Gonzalo Navarro, "A Guided Tour to Approximate String Matching," ACM Computing Surveys, vol. 33, No. 1, pp. 31-88, Mar. 2001.

* cited by examiner

*Primary Examiner*—Carolyn L. Smith
(74) *Attorney, Agent, or Firm*—Ryan, Mason & Lewis, LLP

(57) ABSTRACT

A system for screening nucleotide sequences, a method therefor, a program, a recording medium, and a server on which the screening of nucleotide sequences is executed. The solution comprises a step of storing target nucleotide sequence data and a probe nucleotide sequence, a step of generating complementary sequence data from a probe nucleotide sequence that may be bound to the target nucleotide sequence, and storing a maximum acceptable edit distance between the target nucleotide sequence and the probe nucleotide sequence, a step of reading out each nucleotide sequence data and the maximum edit distance from each storing unit, and evaluating the binding possibility of the target nucleotide sequence data and the complementary sequence data in descending order of edit distance, and a step of storing the result of the binding evaluation in a storage unit.

9 Claims, 14 Drawing Sheets

FIG. 1
(a)
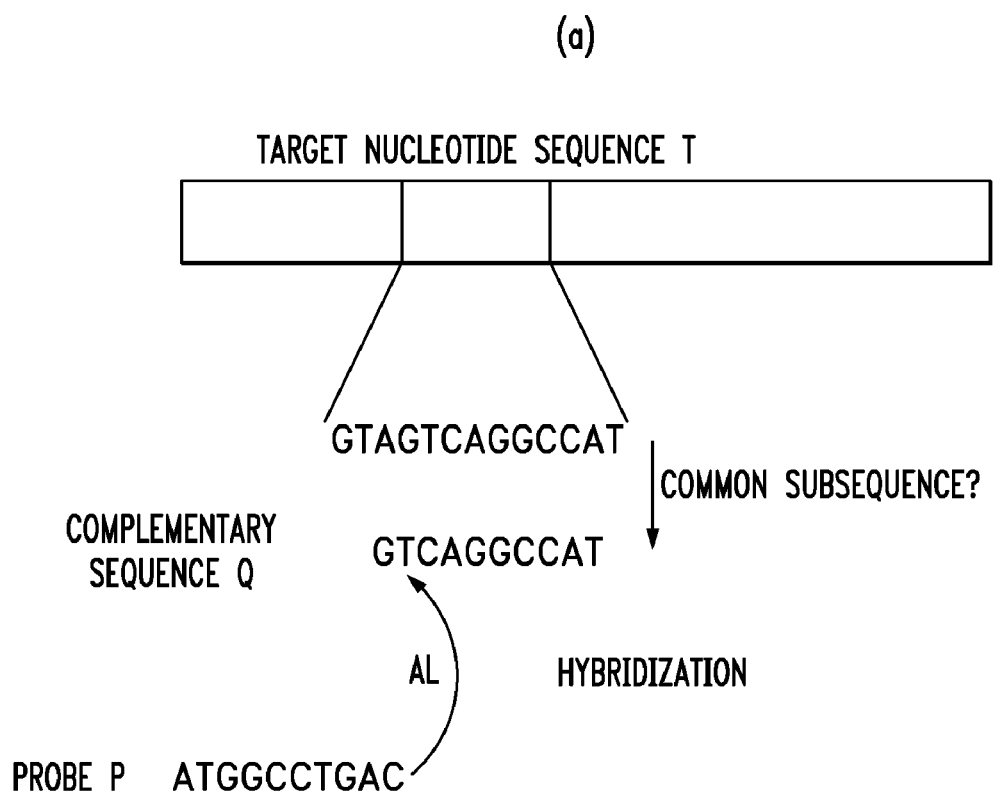
(b)
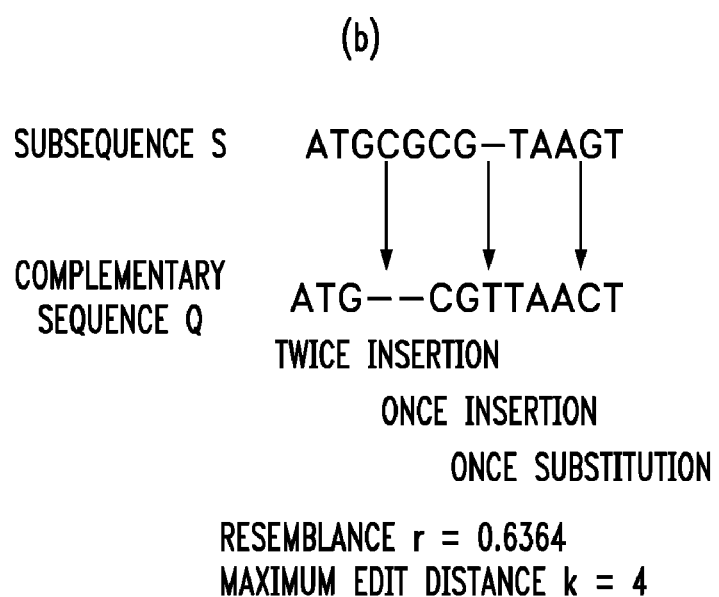

function: largest_prefix_with_common_subsequence(T,Q,k)

FIG. 9

```
//function largest_prefix_with_common_subsequence largest_prefix_with_common_subsequence(sequence T[1..n], sequence Q[1..m], k) {
    for (i=0;i<=k;i++) positions[i] = 0;
    min_k = 0;
    for (probe_position=1; probe_position<=m; probe_position++) {
        max_k = min {k, probe_position};
        for (i=max_k; i>=min_k ;i--) {
            if (i==0 {
                    positions[i] = next_char_position(T, positions[i]+1, Q[probe_position]);
            } else {
                    positions[i] = min { next_char_position(T, positions[i]+1, Q[probe_position]),
                                    positions[i-1] }
            }
            if (positions[i] > n) {
                    min_k = i+1;
            }
        }
        if (min_k > k) {
            ① Absence of common subsequence with length of m-k or longer
            return m+1;
        }
    }
    ② Presence of common subsequence with length of m-min_k or longer
    return positions(k)
```

FIG. 10

```
//function check_target check_target(sequence T[1..n], sequence Q[1..m],k, overlap_length, check_length) {
    position=1;
    while(position <= n) {
        length = largest_prefix_length_with_common_subsequence(
                            T[position..n], Q[1..m], k);
        if (length < check_length) {
            if (check_exactly(
                        T[position..(min(n, position+check_length))], Q, k)) {
                position = position + check_length;
            } else {
                return ("T binds to P")
            }
        } else if (length -1 <= n - position + 1){
            position = position + length - overlap_length - 1;
        } else {
            position = n+1;
        }
    }
    return ("T does not bind to P");
}
```

FIG. 11

|  | 1 | 2 | 3 | 4 | 5 | 6 | 7 | 8 |
|---|---|---|---|---|---|---|---|---|
| POSITIONS[0] | 2 | 3 | 5 | - | - | - | - | - |
| POSITIONS[1] | 0 | 1 | 3 | 5 | 6 | 7 | 8 | - |
| POSITIONS[2] | - | 0 | 1 | 3 | 5 | 6 | 7 | 8 |
| POSITIONS[3] | - | - | 0 | 1 | 3 | 5 | 6 | 7 |

FIG. 12
(a)
EDIT DISTANCE k=3; positions[0]
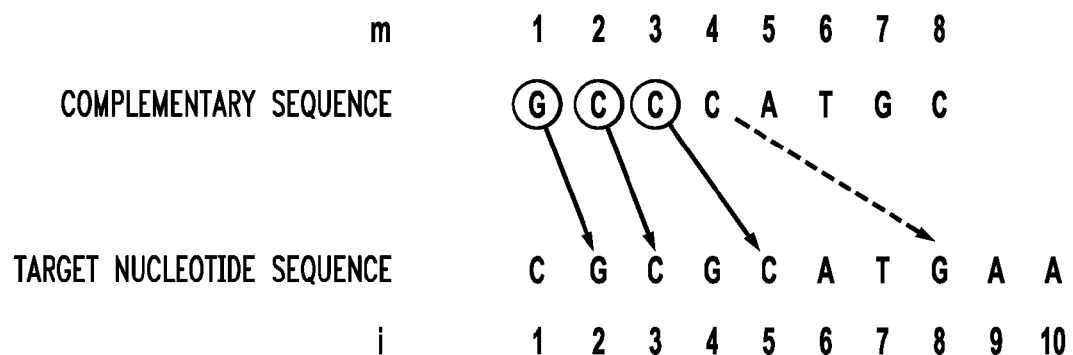
[positions[0],m]= (positions[0], 2, 3, 5, -, -, -, -, -)
(b)
EDIT DISTANCE k=3; positions[1]
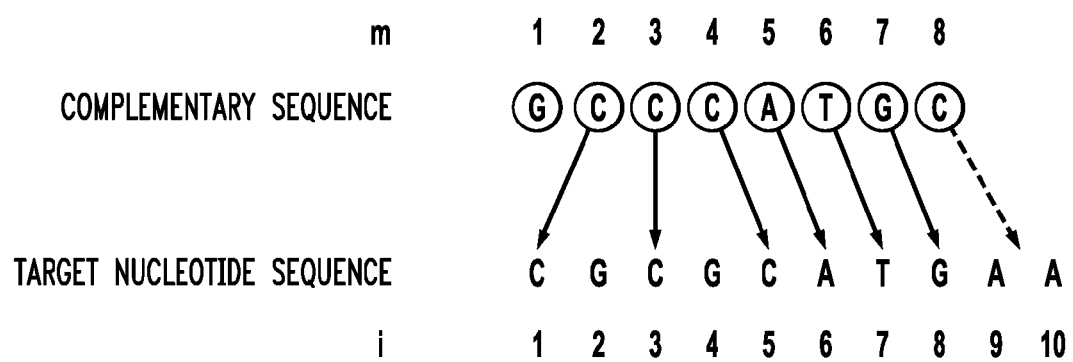
[positions[1],m]= (positions[1], 1, 3, 5, 6, 7, 8)

FIG. 16
| EXAMPLE | | | | COMPARATIVE EXAMPLE |
| --- | --- | --- | --- | --- |
| RESEMBLANCE | | | | Smith-Waterman |
| 0.80 | 0.85 | 0.90 | 0.95 | ---- |
| 405.47s | 284.12s | 136.20s | 45.05s | 1108.33s |
FIG. 17
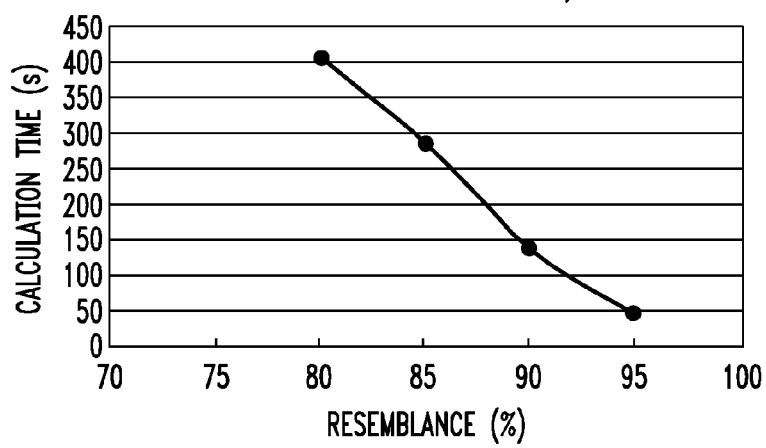
FIG. 18
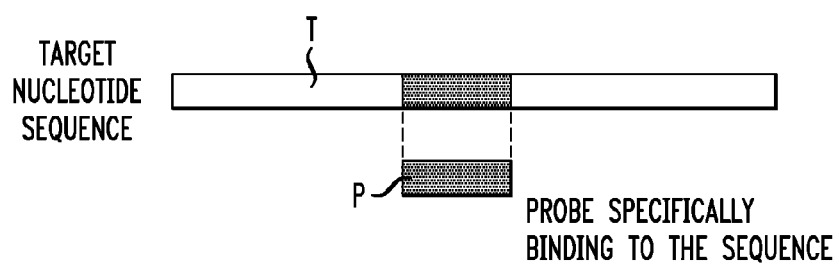

NUCLEOTIDE SEQUENCE SCREENING

CROSS REFERENCE TO RELATED APPLICATIONS

This application is a divisional application under 37 CFR §1.53(b) of U.S. application Ser. No. 10/783,807 filed Feb. 20, 2004, incorporated by reference herein.

FIELD OF THE INVENTION

The present invention relates to screening of nucleotide sequences. More specifically, it relates to a system for screening for a predetermined nucleotide sequence to efficiently determine whether or not the predetermined nucleotide sequence constitutes a portion of another nucleotide sequence; a method therefor; a program causing a computer to execute the method; a computer-readable recording medium storing the program; and a server on which screening of nucleotide sequences is executed through a network.

BACKGROUND OF THE INVENTION

It is known that DNA (deoxyribonucleic acid) is a chain of nucleotides consisting of 4 types of nucleotides; A (adenine), T (thymine), C (cytosine), and G (guanine), and that RNA (ribonucleic acid) is comprised of 4 types of nucleotides; A, U (uracil), G, and C. It is also known that all of these 5 types of nucleotides specifically bind to one another in combinations called complementary base pairing. This is to say, adenine (A) pairs with thymine (T) (in the case of RNA, however, adenine (A) pairs with uracil (U)), and cytosine (C) pairs with guanine (G), so that each of these base pairs forms a double strand. This double strand is referred to as "hybridization", and the generation of a double strand is referred to as "to hybridize". Moreover, a nucleotide sequence that can be bound to a given nucleotide sequence to form a double strand is referred to as a "complementary sequence".

In some cases, it is required to use the above described complementarity of nucleotides to determine whether or not DNA or RNA of interest is present in a sample that is likely to contain predetermined types of DNA or RNA (hereinafter, a nucleotide sequence that is a target of testing is referred to as a target nucleotide sequence in the present invention). Moreover, there may also be a need to prepare a chain of nucleotides that is referred to as a probe in the present invention and that specifically binds to nucleotides in a given region of DNA or RNA, so as to determine whether or not the chain of nucleotides binds to, that is, hybridizes with, the target sequence. The above determination is referred to as binding determination or hybridization determination. Furthermore, a complementary sequence used to detect a target nucleotide sequence is referred to as a probe.

The above binding determination is used for various purposes. For example, a DNA chip is an information processing chip, which uses the above described character of hybridization. In many cases, the information processing chip prepares sequences complementary to the nucleotide sequences of various types of DNA or RNA and simultaneously carries out a large volume of hybridization determination, thereby executing a process of interest. Moreover, what is called PCR (Polymerase Chain Reaction) is a method for determination and evaluation of a DNA sequence by generating sequences complementary to the sequences of two portions on the DNA sequence and copying in large quantities a region surrounded by these complementary sequences.

In many cases of determination and evaluation using these complementary sequences, sequences of DNA or RNA that differ from those of interest may be mixed in an actual target sample. In such a case, assuming that a probe to be prepared or provided does not bind to the mixed nucleotide sequences can provide the efficiency, high precision and high reliability of the determination and evaluation. In some cases, a DNA or RNA synthesizer may be used to prepare a probe P that is specific for a given DNA. Thus, it is considered that the efficiency of protein synthesis, screening and the like is significantly increased by efficiently eliminating probes P other than that of interest.

FIG. 18 is a view showing the relationship between a target nucleotide sequence and a probe. In the figure, the target nucleotide sequence is represented by a symbol T, and the probe is represented by a symbol P. The target nucleotide sequence T can be, for example, a long chain nucleotide sequence in which several thousands of nucleotides are bound (hereinafter, the number of nucleotides is referred as base pair (bp) in the present invention). Substantially, it is ideal that a probe 102 shown in FIG. 18 can be a sequence completely complementary to the sequence of a region represented by Tp in the target nucleotide sequence T.

However, in reality, a predetermined nucleotide sequence binds to another nucleotide sequence that is not completely complementary (the sequences bind to each other with an identity of 80% to 90%). Moreover, nucleotide sequence determination devices such as a sequencer may cause analytical errors. So, it is not appropriate to eliminate nucleotide sequences for the reason that they are not 100% identical and so they cannot be probe candidates. To confirm that the probe P does not bind to the target nucleotide sequence, it has conventionally been required to analyze the nucleotide sequences of both parties by a high precision alignment algorithm such as in the Smith-Waterman method, and to assure that, in the target nucleotide sequence, there are no sequences that are similar to the complementary sequence of the probe.

High-speed searching algorithms such as BLAST (Altchul S F., Miller, G W., Myers E W., Lipman D J., "Basic local alignment search tool", J. Mol. Biol. 1990, Oct. 5, 215 (3), 403-410) or FASTA (Pearson, W R., Lipman, D J., "Improved tools for biological sequence comparison", Proc. Natl. Acad. Sci. USA, 1988, April; 85(8), 2444-2448 Related Articles, Links) have been proposed as means of searching for nucleotide sequences that are similar to each other. However, even using these algorithms, it is not possible to discover all similar partial sequences in the above described target nucleotide sequence, and therefore they are not suitable for screening to assure that the probe does not bind to the target sequence.

SUMMARY OF THE INVENTION

The present invention provides techniques for screening of nucleotide sequences.

To solve the above and other problems, the present invention may quickly provide the user with the evaluation result that a probe P at least does not bind to a target nucleotide sequence T. This is to say, if the information that the probe P at least does not bind to the target nucleotide sequence T can be provided to the user, information regarding effectiveness and reliability of the probe can quickly be provided to the user. Various searching methods have been previously proposed. Information regarding whether or not a probe binds to a given target nucleotide sequence within a range of errors that the user accepts has been essential. However, in a case where the probe binds to the target nucleotide sequence, in addition to the above information, there have also been a need for a nucleotide sequence screening system capable of providing the user with the sequence of a possible probe P; a method therefor; a program causing a computer to execute the method; a computer-readable storage medium on which the program is recorded; and a server therefor. The present invention provides these and other features.

The present invention provides that high-speed screening for a probe can be carried out by providing the user with the information that a probe P at least does not bind to a target nucleotide sequence T with the precision that the user requires, and also information regarding binding possibility, similarity, and the corresponding subsequence, if there is binding possibility in an acceptable range designated by the user.

By way of example, in the present invention, the user designates the maximum edit distance, starts evaluation from an evaluation of whether or not only the maximum edit distance is different, and then evaluates the binding between the probe P and the target nucleotide sequence T in descending order. At the time when it is found that edit distance becomes greater than the maximum edit distance designated by the user, information regarding "non binding" can be provided without carrying out the evaluation of the entire target nucleotide sequence. Moreover, by dynamically altering evaluation termination conditions in response to the nucleotide difference existing between a subsequence and a complementary sequence Q, when it is determined that there is a binding possibility, the present invention provides the user with additional data such as their similarity or nucleotide sequences.

Furthermore, the present invention may improve precision so as to reliably provide high-speed and high-precision screening for a long chain target nucleotide sequence. That is, in another embodiment of the present invention, the target nucleotide sequence is divided into partial sequences Tp having a certain overlap, and it is determined that the target nucleotide sequence does not bind to the probe P on the basis of every partial sequence Tp. More specifically, a target nucleotide sequence T to be evaluated is divided into several partial sequences Tp (p=1 to w) having a certain level of overlap. On the basis of every divided partial sequence Tp, the determination regarding whether or not a sequence complementary to the sequence of the probe P is comprised in the partial sequences Tp is carried out, so as to increase reliability. Still further, the method of the present invention can also be applied for chain length in the case of dividing the target nucleotide sequence into the partial sequences Tp.

That is to say, the present invention provides a computer system for screening nucleotide sequences, which comprises:

a target nucleotide sequence storing unit for storing target nucleotide sequence data;

a complementary sequence data storing unit for generating complementary sequence data from a probe nucleotide sequence that may be bound to the target nucleotide sequence and storing it;

an evaluation processing unit for evaluating the above target nucleotide sequence data and the above complementary sequence data in descending order of edit distance, and determining the binding possibility of the above probe nucleotide sequence to the above target nucleotide sequence; and a storage unit for storing the evaluation result obtained by the above evaluation processing unit.

The above computer system of the present invention preferably comprises a maximum edit distance storing unit for storing a maximum acceptable edit distance between the above target nucleotide sequence and the above probe nucleotide sequence.

The above evaluation processing unit of the present invention may comprise a termination-determining unit for dynamically determining termination of the evaluation, and the above termination-determining unit determines whether the evaluation of the above complementary sequence data is carried out over the above maximum edit distance.

The present invention provides a computer system for screening nucleotide sequences, which comprises:

a target nucleotide sequence storing unit for storing target nucleotide sequence data;

a complementary sequence data storing unit for generating complementary sequence data from a probe nucleotide sequence that may be bound to the target nucleotide sequence and storing it;

an evaluation processing unit for designating a partial short chain sequence from the above target nucleotide sequence data, as well as evaluating the above complementary sequence data on the basis of every the above partial sequence in descending order of edit distance, and determining the binding possibility of the above probe nucleotide sequence to the above target nucleotide sequence; and a storage unit for storing the evaluation result obtained by the above evaluation processing unit.

The present invention provides a method for controlling a computer, which causes a computer system to execute screening of nucleotide sequences, the above method causing a computer system to execute:

a step of storing target nucleotide sequence data and a probe nucleotide sequence;

a step of generating complementary sequence data from a probe nucleotide sequence that may be bound to the target nucleotide sequence and storing it;

a step of storing a maximum acceptable edit distance between the above target nucleotide sequence and the above probe nucleotide sequence;

a step of reading out the above each nucleotide sequence data and the above maximum edit distance from each storing unit, and evaluating the binding possibility of the above target nucleotide sequence data and the above complementary sequence data in descending order of edit distance; and a step of storing the result of the above evaluation in a storage unit.

The present invention provides a method for controlling a computer, which causes a computer system to execute screening of nucleotide sequences, the above method causing a computer system to execute:

a step of storing target nucleotide sequence data and a probe nucleotide sequence;

a step of generating complementary sequence data from a probe nucleotide sequence that may be bound to the target nucleotide sequence and storing it;

a step of storing a maximum acceptable edit distance between the above target nucleotide sequence and the above probe nucleotide sequence;

a step of designating a partial short chain sequence from the above target nucleotide sequence data, as well as evaluating the above complementary sequence data on the basis of every above partial sequence in descending order of edit distance, and evaluating the binding possibility of the above probe nucleotide sequence to the above target nucleotide sequence; and a step of storing the result of the above evaluation in a storage unit.

The present invention provides a computer executable program for a method for controlling a computer, which causes a computer system to execute screening of nucleotide sequences, the above program controlling the above computer system and causing it to execute:

a step of storing target nucleotide sequence data and a probe nucleotide sequence;

a step of generating complementary sequence data from a probe nucleotide sequence that may be bound to the target nucleotide sequence and storing it;

a step of storing a maximum acceptable edit distance between the above target nucleotide sequence and the above probe nucleotide sequence;

a step of reading out each piece of the above nucleotide sequence data and the above maximum edit distance from each storing unit, and evaluating the binding possibility of the above target nucleotide sequence data and the above complementary sequence data in descending order of edit distance; and a step of storing the result of the above evaluation in a storage unit.

The present invention provides a computer executable program for a method for controlling a computer, which causes a computer system to execute screening of nucleotide sequences, the above program controlling the above computer system and causing it to execute:

a step of storing target nucleotide sequence data and a probe nucleotide sequence;

a step of generating complementary sequence data from a probe nucleotide sequence that may be bound to the target nucleotide sequence and storing it;

a step of storing a maximum acceptable edit distance between the above target nucleotide sequence and the above probe nucleotide sequence;

a step of designating a partial short chain sequence from the above target nucleotide sequence data, as well as evaluating the above complementary sequence data on the basis of every the above partial sequence in descending order of edit distance, and evaluating the binding possibility of the above probe nucleotide sequence to the above target nucleotide sequence; and a step of storing the result of the above evaluation in a storage unit.

The present invention provides a computer-readable storage medium on which a computer executable program is recorded for a method for controlling a computer for causing a computer system to execute screening of nucleotide sequences, the above program controlling the above computer system and causing it to execute:

a step of storing target nucleotide sequence data and a probe nucleotide sequence;

a step of generating complementary sequence data from a probe nucleotide sequence that may be bound to the target nucleotide sequence and storing it;

a step of storing a maximum acceptable edit distance between the above target nucleotide sequence and the above probe nucleotide sequence:

a step of reading out each piece of the above nucleotide sequence data and the above maximum edit distance from each storing unit, and evaluating the binding possibility of the above target nucleotide sequence data and the above complementary sequence data in descending order of edit distance; and a step of storing the result of the above evaluation in a storage unit.

The present invention provides a computer-readable storage medium on which a computer executable program is recorded for a method for controlling a computer for causing a computer system to execute screening of nucleotide sequences, the above program controlling the above computer system and causing it to execute:

a step of storing target nucleotide sequence data and a probe nucleotide sequence;

a step of generating complementary sequence data from a probe nucleotide sequence that may be bound to the target nucleotide sequence and storing it;

a step of storing a maximum acceptable edit distance between the above target nucleotide sequence and the above probe nucleotide sequence;

a step of designating a partial short chain sequence from the above target nucleotide sequence data, as well as evaluating the above complementary sequence data on the basis of every the above partial sequence in descending order of edit distance, and evaluating the binding possibility of the above probe nucleotide sequence to the above target nucleotide sequence; and a step of storing the result of the above evaluation in a storage unit.

The present invention provides a server on which screening of nucleotide sequences is executed through the network, the above server comprising:

a database for storing target nucleotide sequence data;

a sending and receiving unit for receiving target designation data and a probe nucleotide sequence that may be bound to the target nucleotide sequence through the network, as well as sending the result of the screening through the above network;

a complementary sequence data storing unit for generating complementary sequence data from the above probe nucleotide sequence and storing it; and an evaluation processing unit for searching through the above database using the above target designation data, evaluating the searched target nucleotide sequence data and the above complementary sequence data in descending order of edit distance, and determining the binding possibility of the above probe nucleotide sequence to the above target nucleotide sequence, as well as transmitting the result to the above sending and receiving unit.

These and other objects, features and advantages of the present invention will become apparent from the following detailed description of illustrative embodiments thereof, which is to be read in connection with the accompanying drawings.

BRIEF DESCRIPTION OF THE DRAWINGS

FIG. 1 is a view showing the relationship among the target nucleotide sequence, GTAGTCAGGCCAT (SEQ ID NO: 3), the probe, ATGGCCTGAC (SEQ ID NO: 1), the complementary sequence, GTCAGGCCAT (SEQ ID NO: 2)/ATGCGT-TAACT (SEQ ID NO: 5) and subsequence, ATGCGCG-TAAGT (SEQ ID NO: 4), of the present invention;

FIG. 9 shows the pseudo-code of the program of the present invention, which causes a computer system to execute a step of evaluating binding possibility;

FIG. 10 shows the pseudo-code of a program, which designates a partial sequence to evaluate binding possibility, in the second embodiment of the present invention;

FIG. 11 is a view showing an embodiment regarding the output data structure of evaluation results in the present invention;

FIG. 12 is a view showing processes that are carried out by the pseudo-code shown in FIG. 9 to obtain evaluation results for a target nucleotide sequence, CGCGCATGAA (SEQ ID NO: 6), in the present invention;

FIG. 16 is a view showing the result of an example of the present invention as well as that of comparative example;

FIG. 17 is a view in which the results of both the example and the comparative example of the present invention are plotted, and the time required to obtain the evaluation results is compared between the example and the comparative example with a similarity unit of 100%; and FIG. 18 is a view showing the relationship between a target nucleotide sequence and a probe.

DETAILED DESCRIPTION OF PREFERRED EMBODIMENTS

Figure 2:
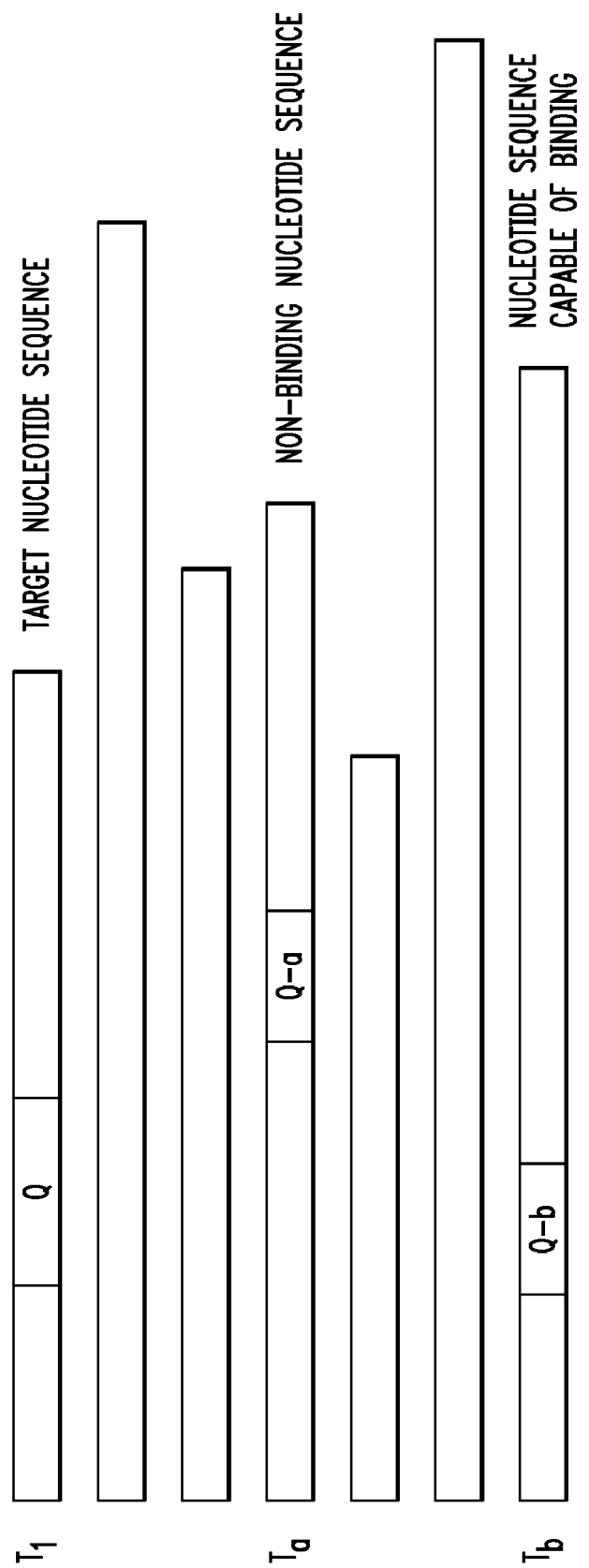
FIG. 2 is a schematic view showing an embodiment in which the screening for a target nucleotide sequence of the present invention is carried out.

The present invention will be further described in the following specific embodiments that are shown in the drawings. However, the below-mentioned embodiments are provided for illustrative purposes only, and are not intended to limit the scope of the invention. In the binding determination of the present invention, computer processable target nucleotide sequence data obtained from a target nucleotide sequence is hereinafter referred to as a target nucleotide sequence T, and computer processable nucleotide sequence data obtained from the nucleotide sequence of a probe is hereinafter referred to as a probe P. In addition, the computer processable complementary sequence data of the probe P is referred to as a complementary sequence Q.

A. General Description of Parameter Used in the Present Invention and Essential Process FIG. 1 is a view showing the relationship among a target nucleotide sequence T, a probe P, and a complementary sequence Q. As shown in FIG. 1(a), in a specific embodiment of the present invention, if the probe P is defined as P=ATGGCCTGAC (SEQ ID NO: 1), Q that is a sequence complementary to P is defined as Q=GTCAGGCCAT (SEQ ID NO: 2). It should be noted that, as shown in FIG. 1(a), the relationship between the probe P and the complementary sequence Q is such that not only each nucleotide of the probe P is substituted by each complementary nucleotide in the complementary sequence Q, but also the complementary sequence Q is opposite in direction to the probe P as shown with an arrow AL. Moreover, it is the process of the evaluation of the present invention that the complementary sequence Q is a sequence portion, which constitutes a portion of the target nucleotide sequence T in the maximum edit distance designated by the user, where T is defined as T=GTAGTCAGGCCAT (SEQ ID NO: 3).

Meanwhile, a similarity r is defined between the target nucleotide sequence T and the probe P or complementary sequence Q in the present invention. In order that the target sequence T binds to the probe P, the present invention provides that at least the target sequence T contains a sequence portion, which has a similarity of r or greater with the probe P. This is to say, in the present invention, unless the target nucleotide sequence T contains a sequence portion with a similarity of r, the target nucleotide sequence cannot bind to the probe P.

Various methods can be applied to determine the similarity r. In the present invention, the similarity r can specifically be determined according to the following standard. When a sequence portion contained in the target nucleotide sequence T is defined as a subsequence S, at least total of k times of character analyzing and determining processing such as substitution, deletion or insertion of nucleotides is required to generate the complementary sequence Q from the subsequence S. The value k can be referred to as the maximum edit distance between the subsequence S and the complementary sequence Q. Herein, if the nucleotide chain length of the complementary sequence Q to the probe P is defined as m, the similarity r can be defined as $r=(m-k)/m$. Accordingly, an "similarity of r or greater" corresponds that, referring to the above formula regarding r, a subsequence S and a complementary sequence Q are designated, whose maximum edit distance is $m(1-r)$ or shorter.

FIG. 1(b) is a view showing a step of determining the above described edit distance, using a specific embodiment. The figure shows an embodiment in which the subsequence S=ATGCGCGTAAGT (SEQ ID NO: 4) and the complementary sequence Q=ATGCGTTAACT (SEQ ID NO: 5). In the embodiment shown in FIG. 1(b), the edit distance between the subsequence S and the complementary sequence Q is 4, and the similarity $r=(11-4)/11=0.6364$. FIG. 1(b) shows each of a partial sequence Tq and the complementary sequence Q in a proper alignment (hereinafter, the above-described step is referred to as an alignment). In the embodiment shown in FIG. 1(b), since deletion takes place twice and each of substitution and insertion takes place once, the edit distance is 4.

In the present invention, if more than (m−k) nucleotides of a complementary sequence Q do not appear in the same order on a predetermined target nucleotide sequence T, it can be said that there are no target nucleotide sequences T, whose an edit distance from the complementary sequence Q is shorter than k. Since the relationship shown in FIG. 1(a) exists between the probe P and the complementary sequence Q, if information regarding the complementary sequence Q obtained from the probe P and the target nucleotide sequence T can be obtained, the relationship between the probe P and a subsequence S can easily be obtained.

Moreover, in the present invention, a target nucleotide sequence to which a given probe P is likely to bind can be screened. FIG. 2 is a view showing a step of determining the specificity of a complementary sequence Q in the relationship between a partial sequence Tp and the complementary sequence Q in the present invention. In FIG. 2, multiple target nucleotide sequences are prepared as targets of screening. The figure is a schematic view showing an embodiment, in which it is determined whether or not the probe P specifically binds to only the target nucleotide sequence $T_1$. The figure shows that the target nucleotide sequence $T_1$ contains the entire complementary sequence Q of the probe P, and that a target nucleotide sequence Ta also contains a complementary sequence $Q_a$ just at an edit distance of (m−a) (wherein a is a positive integer greater than k). In addition, a target nucleotide sequence $T_b$ contains a partial sequence having an edit distance of (m−b) (wherein b is a positive integer smaller than k). Consequently, it is shown that the probe is likely to bind to the target nucleotide sequences $T_1$ and $T_b$. In this case, according to the present invention, since similarity with the subsequence and nucleotide sequence length, as well as the information regarding binding possibility are given to the user, it is also possible to design the probe P so as to impart further properties thereto.

B. The Process of the Screening Method of the Present Invention

Figure 3:
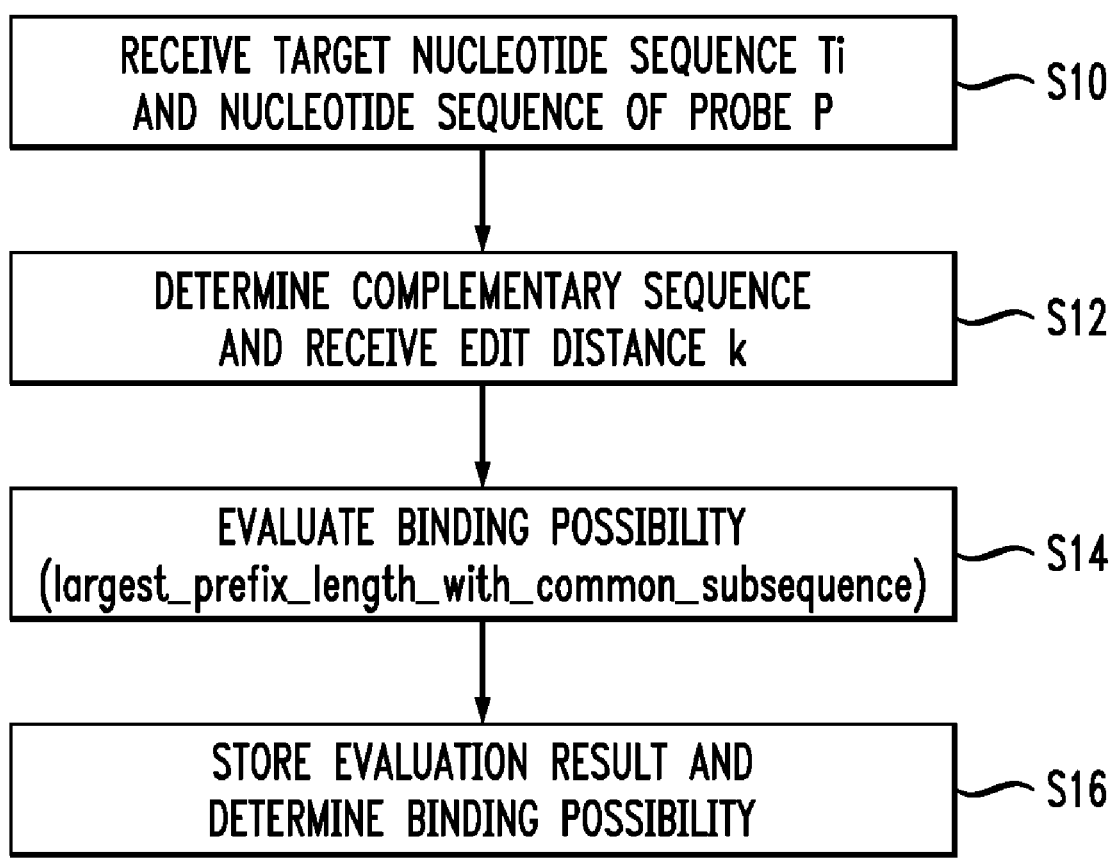
FIG. 3 is a flow chart showing a process in the first embodiment of the screening method of the present invention.

By the efficient use of the above described properties, the present invention enables determination regarding whether or not the target nucleotide sequence is suitable as a probe P and whether or not another probe P should be provided, more rapidly than a high-precision sequential analysis. That is to say, according to the present invention, it can be guaranteed that the probe P does not hybridized with the target nucleotide sequence T. FIG. 3 is a flow chart showing a process of a method of the present invention. As shown in the figure, in the method of screening of nucleotide sequences of the present invention, a nucleotide sequence that is to be a probe P and the target nucleotide sequence T are received in step S10. During the step, a nucleotide sequence that is actually obtained using a sequencer may also be input. Moreover, the probe P can also be synthesized using a nucleotide sequence synthesizer or the like. With regard to the target nucleotide sequence, for example, the user can interactively select it from a database, which stores nucleotide sequences of DNA or RNA, or the user can also use a DNA sample collected from live tissues of mammals, eukaryotic microorganisms or the like. In the screening method of the present invention shown in FIG. 3, the routine then proceeds to step S12, and in this step, a complementary sequence Q is generated from the probe P and then stored in a suitable storage region. At the same time, a maximum edit distance k is received then stored in a suitable storage region.

In step S14, a function, largest_prefix_with_common_subsequene( ), is applied to a target nucleotide sequence T to be tested, and it is determined whether or not the complementary sequence Q is present as a subsequence of the target nucleotide sequence T, which is analyzed at that moment, thereby carrying out evaluation of binding possibility. The routine of the present invention then proceeds to step S16, in which the obtained evaluation result is stored in a suitable storage region of a computer's memory. Moreover, in step S16, the stored evaluation result is read out, determination such as "bind" or "not bind" is carried out, and the result is returned to the user, so that the determination result is provided to the user.

Figure 4:
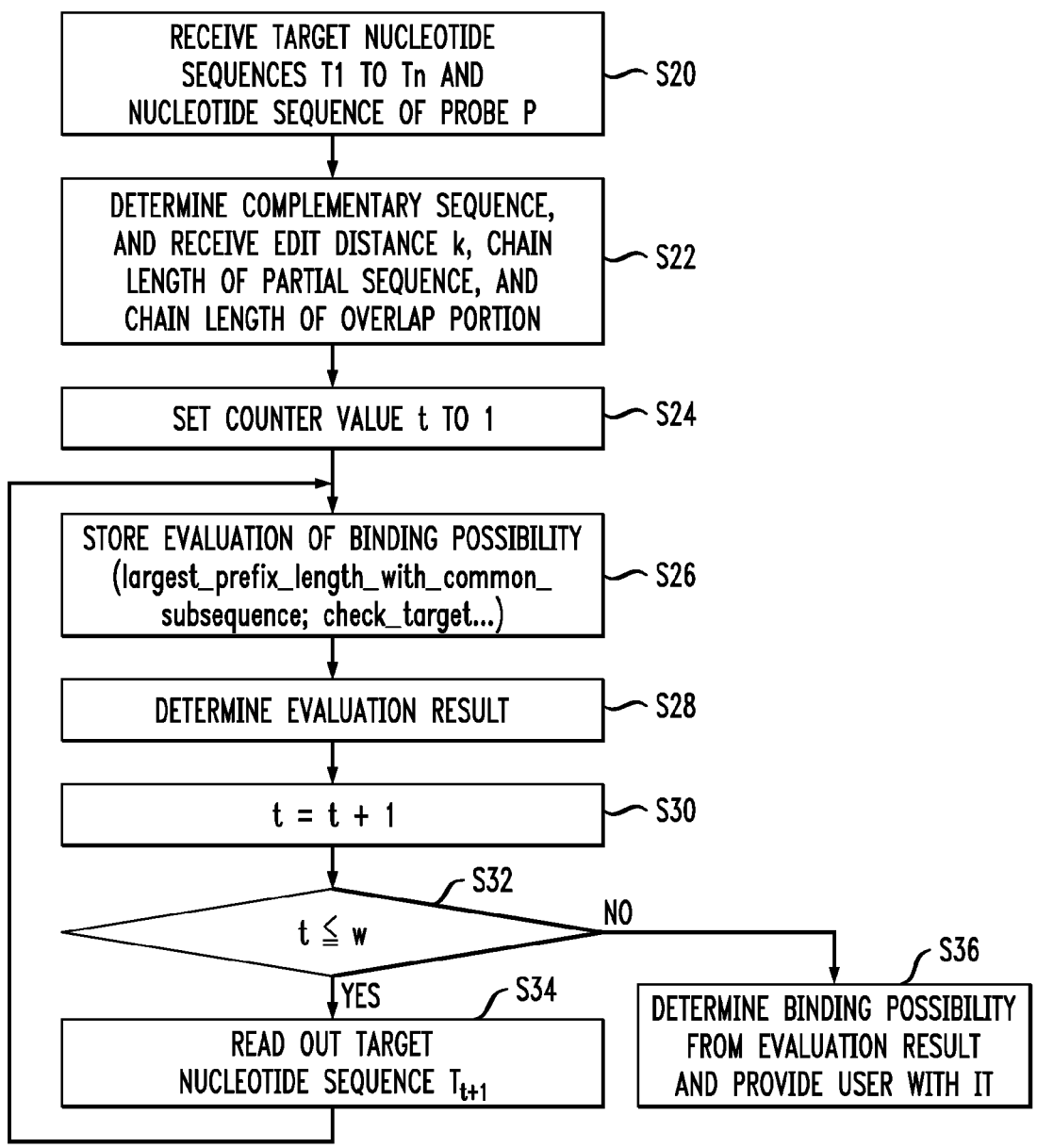
FIG. 4 is a flow chart showing a process in the second embodiment of the screening method of the present invention.

FIG. 4 is a flow chart showing a process in the second embodiment of the screening method of the present invention. In the embodiment shown in FIG. 4, a target nucleotide sequence T exists as multiple target sequences $T_1$ to $T_w$. The evaluation result is prepared on the basis of every target nucleotide sequence, and it is stored in a storage region. In the embodiment shown in FIG. 4, in step S20, a nucleotide sequence that is to be a probe P and a multiple number of target nucleotide sequences $T_1$ to $T_w$ are received, and they are stored in their respective storing units. In step S22, a complementary sequence Q is determined from the probe P, and further, the inputs of variables such as an edit distance k, the unit of length of partial sequences with which evaluation is repeatedly carried out (length), and the length of overlap (overlap_length) are received. A counter t is set to 1 in step S24, and binding evaluation is carried out on the target nucleotide sequence in step S26. In step S26, the target nucleotide sequence is evaluated, and the result is stored in a storage unit. In step S28, information regarding the presence or absence of a subsequence capable of binding is obtained by making access to the evaluation results.

The counter t is incremented in step S30, and it is determined whether or not t is smaller than w in step S32. When t≦w (yes) is the determination in step S32, the routine proceeds to step S34. In the step, a target nucleotide sequence $T_{t+1}$ is read out from the storage region, and the routine then returns to step S26. In the step, the evaluation result of the target nucleotide sequence $T_{t+1}$ is prepared and stored. When t>w (no) is the determination in step S32, since evaluation of the target nucleotide sequence to be evaluated has been terminated, the routine proceeds to step S36. In the step, evaluation result is obtained, and binding possibility determined from the result is then provided to the user.

Figure 5:
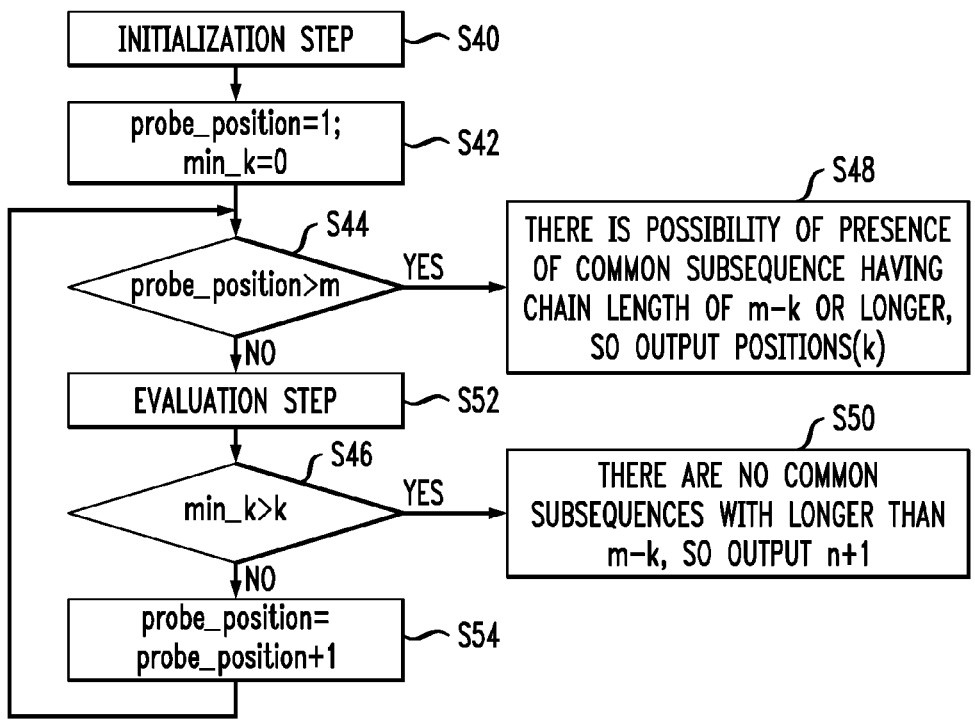
FIG. 5 is a schematic flow chart showing a step of evaluating binding possibility in the present invention.

FIG. 5 is a view showing a flow chart of a function largest_prefix_with_common_subsequence( ), which carries out a step of evaluating binding possibility in the present invention. The step of evaluating binding possibility in the present invention as shown in FIG. 5 starts from step S40 of initialization. In the step, the value of positions[i] and the value of an edit distance counter i are initialized. Herein, positions[i] is a function, which returns a value given by a function next_char_position( ), or returns the smaller value of that given by a function next_char_position( ) and that given by a function positions[i−1]. In the function next_char_position( ), the target nucleotide sequence, the edit distance counter i, and a character c representing a nucleotide existing in the complementary sequence are used as arguments. Thus, next_char_position (T, i, c) is a function, which returns the position of the character c that appears first in T[i . . . n], when counting from the top of the nucleotide chain of the target nucleotide sequence T. Moreover, where the nucleotide of the character c does not appear in T[i . . . n], next_char_position (T, i, c) returns a value (n+1).

In step S42, the value of probe_position representing the position of a complementary nucleotide and the value of min_k are initialized. The value of min_k is given as a value showing that there are no edit distances that are smaller than min_k. It is a scale providing the unachievable minimum value of nucleotide between a partial sequence and the complementary sequence Q. That is, min_k=0 means that the subsequence S completely matches the complementary sequence Q. At the same time, min_k is used also as a termination condition value, which is used to carry out determination of termination, and it also gives a scale of nucleotide errors between the probe P and the subsequence S. In step S44, it is determined whether or not the variable probe_position corresponding to the number of nucleotides contained in the complementary sequence Q is greater than m that is the number of nucleotides of the complementary sequence Q. When the variable probe_position is greater than m in the determination in step S44 (yes), since no nucleotides of the complementary sequence are remained to be evaluated, the routine proceeds to step S48. Since the edit distance counter i is greater than min_k in this stage, there still remains a possibility that a subsequence having a chain length of m−k or longer exists. Accordingly, the value of positions[k] is output and stored in the storage unit.

On the other hand, when the variable probe_position is smaller than m in the determination in step S44 (no), an evaluation step shown in step S52 is carried out. In the evaluation step, the value of position[i] is determined, and a step of storing the evaluation result in the storage unit is carried out. This step will be described more in detail later. As stated later, when the evaluation step is terminated by meeting given termination conditions, it is determined whether or not the value of min_k becomes greater than the maximum edit distance k in step S46. When the value of min_k is greater than k (yes), since there are no common subsequences with a chain length of (m−k) or longer, the routine proceeds to step S50. In the step, (n+1) is output as a value of positions[i], and the evaluation step is terminated. The value of "true" in the termination in step S46 is generated as a signal for termination of evaluation. On the other hand, when the value of min_k is smaller than k (no), the routine proceeds to step S54. In the step, the value of probe_position is incremented, and the routine is then returned to step S44, in which the next nucleotide in the complementary sequence Q is evaluated. The routine from steps S44 to S52 is repeated until the determination in step S46 returns a positive result (yes), while dynamically changing the termination conditions in the evaluation step by dynamically changing the value of min_k.

Figure 6:
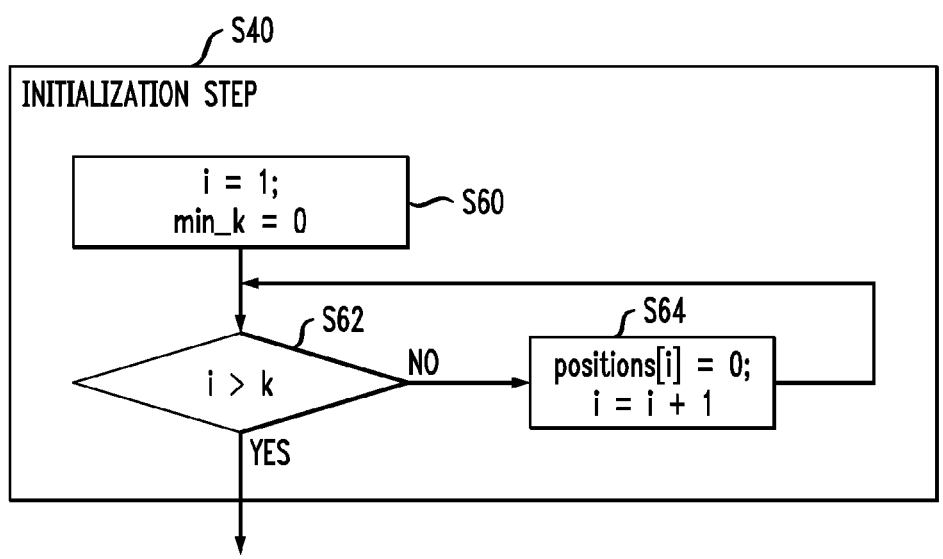
FIG. 6 is a view showing an initialization step that is carried out for a step of evaluating binding possibility in the present invention.

FIG. 6 is a view showing an initialization step as shown in step S40 in FIG. 5. In the initialization step shown in FIG. 6, the edit distance counter i is initialized to 0 in step S60, and in steps S62 and S64, position[i] is set to 0, until the edit distance counter i becomes greater than the maximum edit distance k. At the same time, the edit distance counter i is incremented to i=i+1. This initialization step is carried out so as to reliably set the value of positions[i] to 0 for the edit distance k or shorter.

Figure 7:
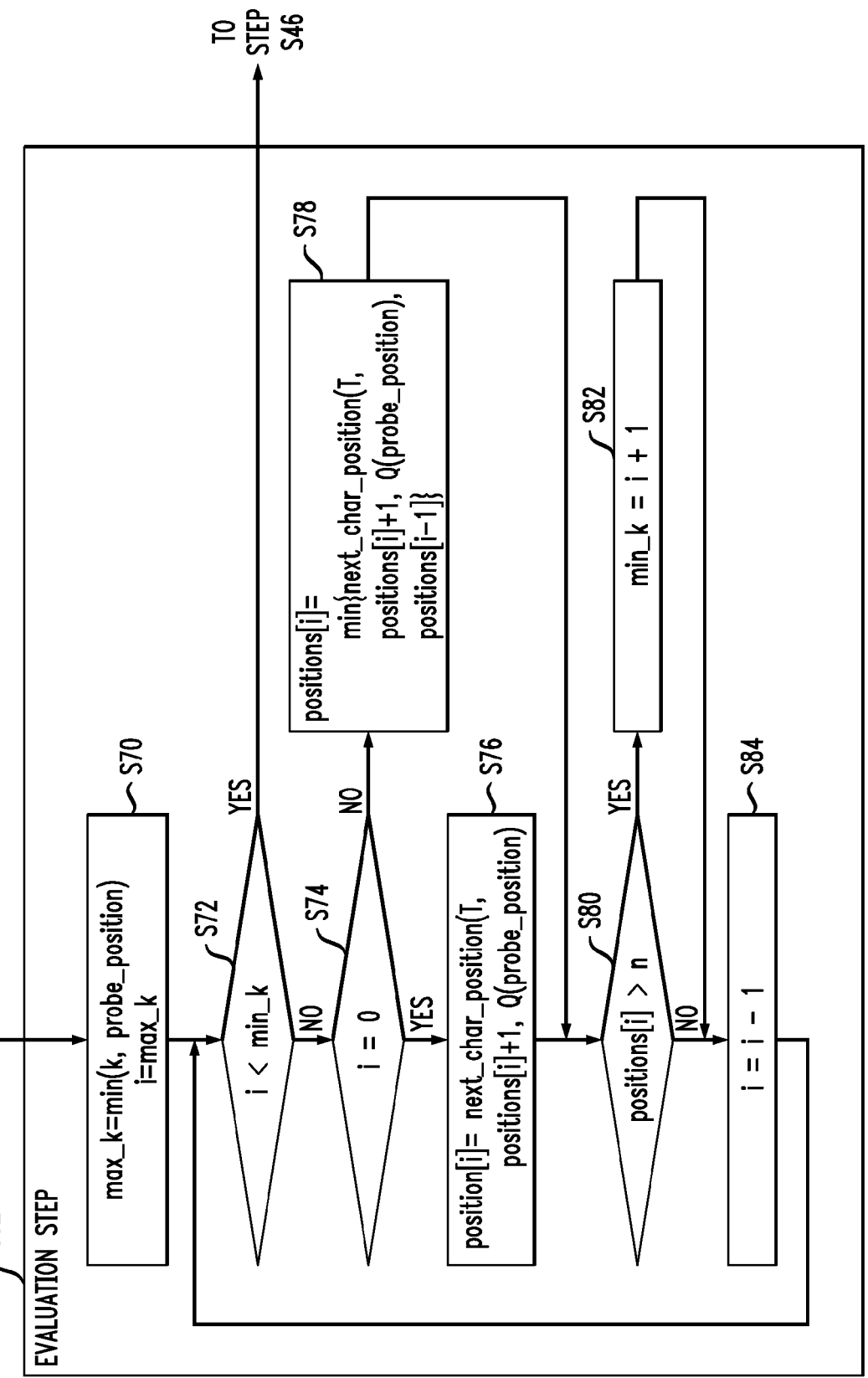
FIG. 7 is a flow chart showing the details of an evaluation step of evaluating binding possibility in the present invention.

FIG. 7 is a flow chart showing the details of the evaluation step in step S52, which is described in FIG. 5. In the evaluation step shown in FIG. 7, in step S70, max_k is set as the smaller value of the maximum edit distance k or the value of probe_position. In step S72, it is determined whether or not the edit distance counter i is smaller than min_k that is a termination condition. When the value of the edit distance counter i is greater than or equal to min_k (no), the routine proceeds to step S74, in which it is determined whether or not the edit distance counter i is 0. In contrast, when it is determined that the edit distance counter i is smaller than min_k in step S72 (yes), the evaluation step is terminated, and the routine branches to step S54.

When the edit distance counter i is 0 in the determination in step S74 (yes), the routine proceeds to step S76, in which the value of positions[i] is given as next_char_position(T, positions[i]+1, Q(probe_position)).

On the other hand, when the edit distance counter i is not 0 in the determination in step S74 (no), the routine branches to step S78, in which the value of positions[i] is set as the smaller value of the value of next_char_position (T, positions[i]+1, Q(probe_position)) and the value of positions[i−1]. Thus, when positions[i] returns a value smaller than or equal to n, the number of nucleotides, that is under evaluation at that time, it means that a matching nucleotide sequence is likely to exist in a given maximum edit distance k. The values of positions[i] calculated in steps S76 and S78 are stored as evaluation results in a suitable storage unit.

Thereafter, the routine proceeds to step S80, and in the step, it is determined whether or not positions[i] becomes greater than n. As stated above, the function next_char_position ( ) returns a value smaller than n that represents the number of nucleotides of the complementary sequence Q, even in a case where there are found no nucleotides corresponding to the nucleotide that is under evaluation. Accordingly, when the value of positions[i] is smaller than or equal to m in the determination in step S80 (no), in order to determine another compatible possibility, the edit distance counter i is set to i=i−1 in descending order in step S84, and the routine is then returned to step S72 to continue the determination. On the other hand, when the determination in step S80 is (yes), the value of positions[i] is given as n+1 from largest_prefix_with_common_subsequence( ) shown in FIG. 5. In step S82, min_k=i+1 is set so as to complete the evaluation step in FIG. 7, and thereafter, the routine is returned to step S84. In step S84, the edit distance counter i is set to i=i−1, and the routine is then returned to step S72. In step S72, a true value (yes) is reliably returned as a determination result. The routine then branches to step S54 shown in FIG. 5, and it is repeated.

Figure 8:
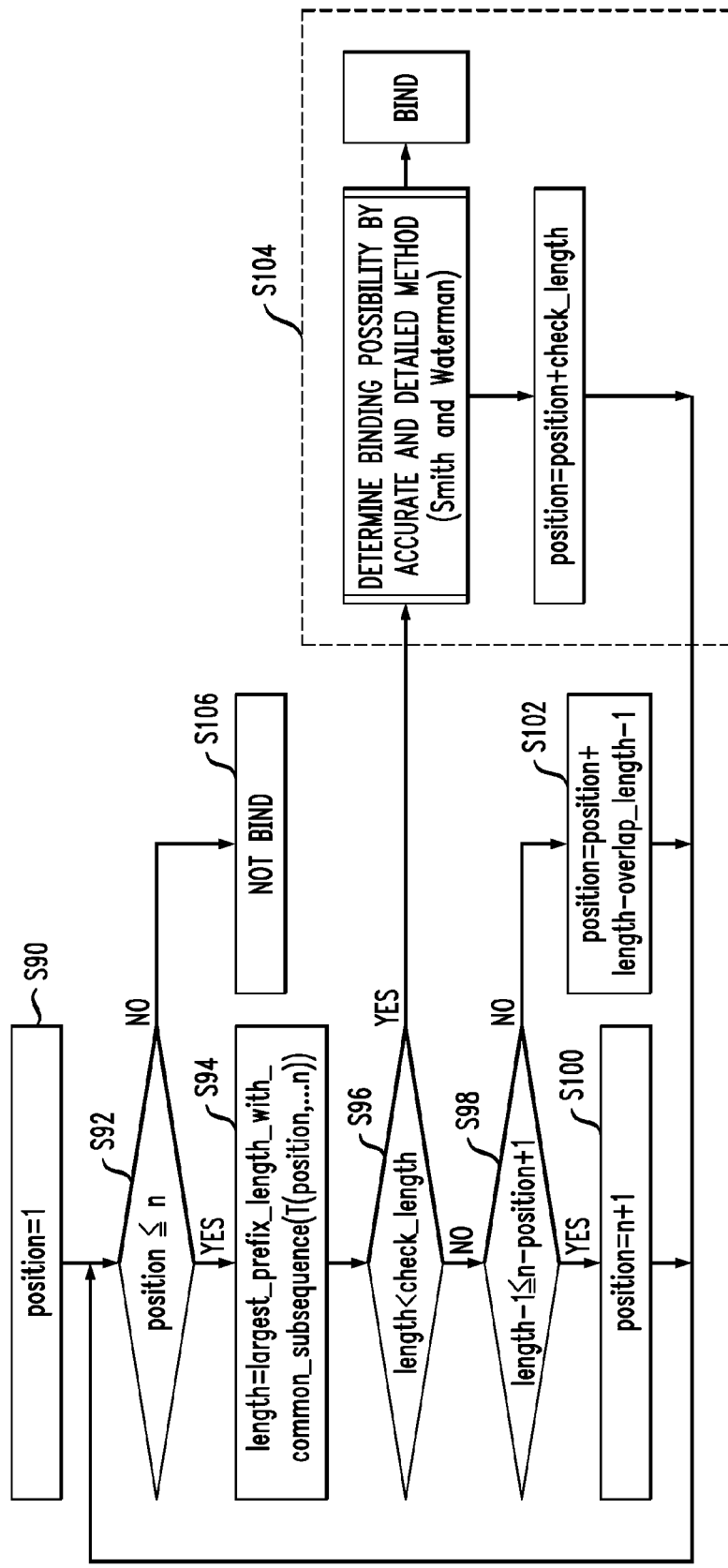
FIG. 8 is a flow chart showing, in detail, a process in the second embodiment of the screening method of the present invention.

FIG. 8 shows an embodiment in which evaluation of a target nucleotide sequence is carried out on the basis of every partial sequence in the screening method of the present invention. In the embodiment shown in FIG. 8, there are defined: a variable "length" defining the given length of a partial sequence to the target nucleotide sequence T; a "position" designating the position of the partial sequence in the target nucleotide sequence; and a variable "overlap_length" that is a variable providing overlap in the terminal portions of partial sequences. In the routine of the screening method of the present invention shown in FIG. 8, the steps shown in FIGS. 5 to 7 can be applied with the exception of evaluation of the nucleotide positions of the target nucleotide sequence on the basis of every partial sequence, using the variables "position", "length", and "overlap_length". Accordingly, only the necessary part of the routine of the present invention of carrying out evaluation on the basis of every partial sequence will be explained below. First, in step S90, the variable "position" designating a partial sequence is initialized. Then, in step S92, it is determined whether or not the variable "position" is smaller than or equal to n. In the determination in step S92, since the variable "position" is always smaller than or equal to n, until the most terminal n of the target nucleotide sequence is evaluated, a true value is obtained by the determination in step S92 (yes). The routine then proceeds to step S94, and the variable "length" is defined therein. The variable "length" can be set in advance in consideration of experimental conditions or the like, or it can also be set by the user's input. In the present invention, as shown in step S94, the variable can also be set, using the returned value of other appropriate functions such as largest_prefix_length_with_common_subsequence( ) shown in FIG. 5.

As stated above, the function largest_prefix_length_with_common_subsequene( ) returns a value of 4 m, when a random and sufficiently long target nucleotide sequence and a random complementary sequence Q are given. In the present invention, the length can be set so as to take an appropriate value without using the above described specific function. Moreover, in the embodiment shown in FIG. 8 also, the edit distance counter i is initialized on the basis of a designated partial sequence, and a partial sequence Tw is used as a target nucleotide sequence T, so that the steps shown in FIGS. 5 to 7 can repeatedly be carried out. In step S96, it is determined whether or not the variable "length" is shorter than "check_length" that is a chain length of nucleotides that are probably capable of binding to each other regardless of the distance between the nucleotides.

When the "length" is determined to be shorter than the "check_length" (yes) in the determination in step S96, the routine proceeds to step S104. In the step, determination regarding binding possibility may be carried out according to a high-precision method such as the Smith-Waterman method (P. D. Smith, M. S. Waterman, Identification of common molecular subsequences. J. Mol. Biol., 147: 195-197, 1981), a new position value may be generated by addition of check_length, and then the routine may return to step S92. During the step, the check_length may be set to a value greater than or equal to m/r. When it is set to a value of 4 m, the determination "there is a binding possibility" is made for all the partial sequences, and the evaluation in step S104 is carried out too frequently, thereby inhibiting the high-speed performance of the present invention. Accordingly, in the present invention, check_length is set to a value between m/r and 4 m, and a value of approximately 2 m is adopted as check_length, so that it often provides a stable result.

On the other hand, when the "length" is determined to be longer than or equal to the "check_length" (no) in step S96, the "length" is compared with the remaining nucleotide chain lengths in step S98. When the "length" is shorter than the remaining nucleotide chain lengths (yes), the routine further proceeds to step S102. In the step, the "length" is added to the nucleotide positions that have been evaluated so far, and considering overlap_length so as to give an appropriate overlap, the next partial sequence is designated. In the embodiment shown in FIG. 8, the routine returns to step S92 again, and the steps S92 to S98 are carried out again. When the "length" is longer than the remaining nucleotide chain lengths (no), position n+1 is set in step S100, and the routine returns to step S92. In this case, a false value is returned by the determination in step S92 (no), and an evaluation result "not bind" is given in step S106.

FIG. 9 shows a pseudo-code, which causes a computer system to execute the steps shown in FIGS. 5 to 7. FIG. 10 shows a pseudo-code for a step of carrying out evaluation on the basis of every partial sequence shown in FIG. 8. A function check_exactly (T, Q, k) shown in FIG. 10 indicates a high-precision determination method that is used in step S102 shown in FIG. 8. Although it takes the same period of time that is conventionally required, the function check_exactly (T, Q, k) determines whether or not the target nucleotide sequence T actually binds to the complementary sequence Q by an accurate calculation according to the Smith-Waterman method or the like. When the target nucleotide sequence T does not bind to the complementary sequence Q, the function returns true, and when the target nucleotide sequence T binds to the complementary sequence Q, the function returns false. In the present invention, the Smith-Waterman method is adopted as a specific example of the method used for check_exactly (T, Q, k). However, any method other than the Smith-Waterman method can be used for the function. In order to provide the determination "not bind" to the user with high precision, the function check_exactly (T, Q, k) can also be set to always return "false". In this case, when the result "not bind" is obtained, it can always be said that the target nucleotide sequence does not bind to the complementary sequence. Therefore, this is useful also for determination of hybridization.

FIG. 11 is a view showing evaluation result obtained by the screening method of the present invention in the form of a table. In the embodiment shown in FIG. 11, the target nucleotide sequence T is CGCGCATGAA (SEQ ID NO: 6), the complementary sequence Q is GCCCATGC, and the edit distance k is 3. The evaluation result obtained by the screening method of the present invention will be explained below with reference to FIG. 11. The vertical column of the table of FIG. 11 represents the value of the edit distance counter i, the lateral column represents the value of probe_position indicating a position in the complementary sequence, and each value in the table represents the value of position[i] at the time of termination of the evaluation step in FIG. 7. In the embodiment shown in FIG. 11, since the maximum edit distance k is 3, calculation is carried out only on those having an edit distance i of 3 or smaller. In the embodiment shown in FIG. 11, the calculation of positions[i, probe_position] finally proceeds to ② of the pseudo-code shown in FIG. 11, and 7 is obtained as a value of positions[3]. Accordingly, 7 is returned as a returned value, and during this routine, the final value of min_k is 2. With regard to the above described positions[i, probe_position], when positions[i, probe_position] is j, the positions[i] becomes probe_position[i,j]. This sequence data may be stored as a table, or as explained in the present invention, only the value of position[i] with respect to the variable of probe_position that is under evaluation may be stored.

FIGS. 12 (a) and (b) schematically show a step of returning the values of positions[0] and positions[1] shown in FIG. 11. As shown in FIG. 12 (a), in the case of positions[0], nucleotides appearing in the complementary sequence Q simply represent the positions of the nucleotides in the target nucleotide sequence, and accordingly, the values given by 2, 3 and 5 are provided as the values of positions[0, m].

On the other hand, in the case of positions[1], when i≧2, the smaller value of the values of next_char_position and positions[i−1] is returned as a returned value. Thus, although the value of positions[0, 1] is 2, since the first cytosine (C) in the complementary sequence Q appears as the first nucleotide in the target nucleotide sequence, the smaller value that is 1 is obtained. Likewise, the second cytosine (C) in the complementary sequence Q appears as the third nucleotide in the target nucleotide sequence T. As the returned value of next_char_position is 3, and the value of the corresponding positions[0, 2] are both 3, the value that is 3 is returned.

Moreover, the fourth nucleotide cytosine (C) in the complementary sequence Q appears at position 5 in the target nucleotide sequence. Similarly, adenine (A), thymine (T) and the seventh guanine (G) in the complementary sequence Q appear at positions 6, 7 and 8 in the target nucleotide sequence, respectively. These numbers constitute the line of positions[1], so that a line consisting of 1, 3, 5, 6, 7 and 8 is provided. Similarly, in the case of position[2], the third nucleotide cytosine (C) in the complementary sequence Q appears at the first position in the target nucleotide sequence T, thereby giving a value of 1. The fourth nucleotide cytosine (C) appears at position 3, and the fifth nucleotide adenine (A) appears at position 6. However, 5 is adopted herein as a value of the corresponding positions[1] on condition that m=4. Although the sixth nucleotide thymine (T) appears at position 7, 6 is adopted herein as a value of the positions[1] on condition that m=5. Accordingly, as shown in FIG. 11, a line consisting of 0, 1, 3, 5, 6, 7 and 8 is provided.

In the case of k=3 that is the embodiment shown in FIG. 11, positions[1] takes a value of 8 at the point of probe_position=7. Accordingly, the value of next_char_position (T, 9, "C") becomes n+1=11, which is greater than n. In the final step of probe_position=8, therefore, the value of min_k is incremented by only 1, so as to provide 2. The value min_k=2 shows that the length of a subsequence common in the target nucleotide sequence and the complementary sequence is m−2=6. Moreover, when the same calculation is carried out, using the same target nucleotide sequence and the same complementary sequence, with a condition of the maximum edit distance k=1, calculations of positions[1] and positions [0] are carried out with the edit distance counter i=0,1, and then evaluation results are obtained, thereby terminating the step. In this case, the calculation proceeds to ① of the pseudo-code, and a value of n+1=11 is returned. This shows that no common subsequences having a length of m−1=7 or longer exist. In the present invention, it is not always necessary to accumulate evaluation results in the form of an evaluation result table as shown in FIG. 11, but as stated above, it is also possible to store only the maximum value of positions [i] in the storage unit in a data form.

C. The Nucleotide Sequence Screening System of the Present Invention

Figure 13:
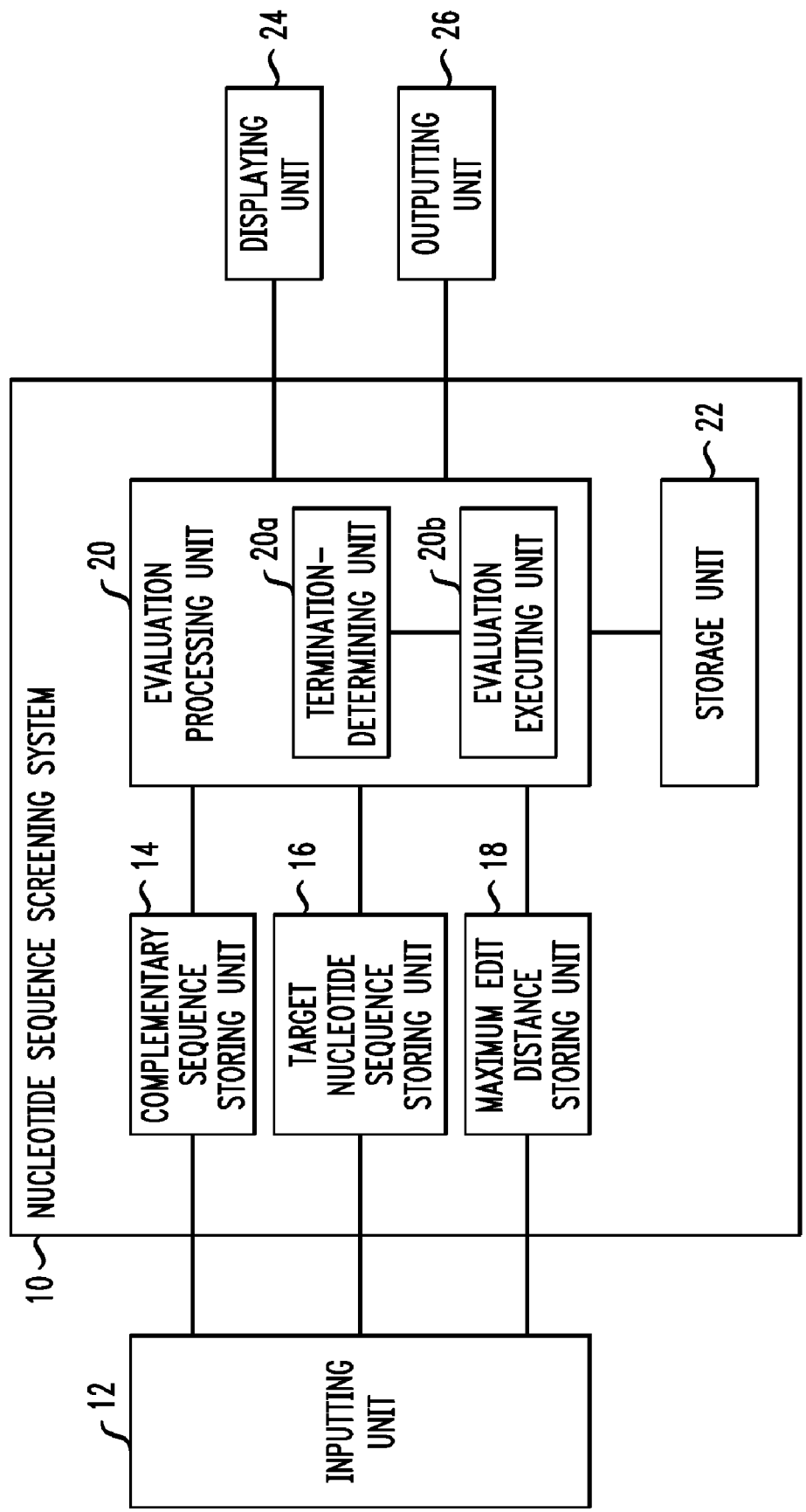
FIG. 13 is a view showing the first embodiment of the nucleotide sequence screening system of the present invention.

FIG. 13 is a function block diagram schematically showing a nucleotide sequence screening system for implementing the screening method of the present invention. A nucleotide sequence screening system 10 (hereinafter, abbreviated to system) shown in FIG. 13 generally comprises a computer comprising a central processing unit (CPU) and necessary storage units. The system carries out an evaluation step for screening by receiving the inputs of a target nucleotide sequence and a complementary sequence.

More specifically, the system 10 of the present invention comprises a complementary sequence storing unit 14, a target nucleotide sequence storing unit 16, a maximum edit distance storing unit 18, and an evaluation processing unit 20. Each of the complementary sequence storing unit 14, the target nucleotide sequence storing unit 16, and the maximum edit distance storing unit 18 is configured as an appropriate memory or memory region. In FIG. 13, these units are described as different blocks so as to clearly describe each function block, but in the present invention, these can also be a memory region, which is divided to a single random access memory or the like for packaging reason. The complementary sequence storing unit 14 receives the input of a probe P from an inputting unit 12, and stores a complementary sequence Q that is generated using a relationship of complementarity. The target nucleotide sequence storing unit 16 and the maximum edit distance storing unit store the inputted target nucleotide sequence data and the maximum edit distance k, respectively. The above inputting unit 12 may comprise a key board, a data readout unit and others in the present invention. The data readout unit reads out the nucleotide sequence of the probe P, which is stored in an input/output medium such as a floppy (registered trade mark) disk, hard disk, CD-ROM or DVD, and sends the data of the probe P to the system of the present invention.

In the evaluation processing unit 20, CPU reads out, from a hard disk (not shown), a program causing the system to execute the screening method of the present invention, and implements it as a function block that is configured as software. The evaluation processing unit 20 is comprised of largest_prefix_with_common_subsequence as shown in FIG. 5. It comprises a termination-determining unit 20a for dynamically terminating evaluation, and an evaluation executing unit 20b. The evaluation processing unit 20 reads out the complementary sequence Q, the target nucleotide sequence T, and the maximum edit distance k from the complementary sequence storing unit 14, the target nucleotide sequence storing unit 16, and the maximum edit distance storing unit 18, respectively, and the unit 20 then carries out evaluation and determination of a common subsequence, using the screening method of the present invention. The termination-determining unit 20a makes comparison between a value of min_k and the maximum edit distance k. When the value of min_k becomes greater than k, the unit determines that there are no sequences that are determined as "bind" in a range that the user requires, and commands the evaluation executing unit 20b not to evaluate probe_position from then on. Receiving this command, the evaluation processing unit 20 writes the calculated evaluation result in a storage unit 22 as a format of position[i, probe_position] in a specific embodiment of the present invention. In the specific embodiment of the present invention, the evaluation result is preferably configured in the form of an evaluation result table as shown in FIG. 11, so as to provide information for the subsequent further evaluation. However, in the present invention, it may also be possible to select only the necessary value of positions[i, probe_position] and store it.

After preparation of an evaluation result table, the evaluation processing unit 20 refers to values of positions[i], looks up a value of positions[i] corresponding to the value of a given probe_position, and determines whether or not a returned value greater than or equal to probe_position is contained in a column corresponding to probe_position. Where probe_position>m and the value of min_k becomes greater than k, it is determined that no common subsequences are found in a range corresponding to the maximum edit distance k required, and a displaying unit 24 displays a determination result as "not bind" to the user. On the other hand, in the case of probe_position>m and min_k<k, min_k=i+1 in the edit distance counter i of the positions[i], and it is determined that there is a common sequence having a sequence length of (m−min_k). Such a determination result is provided to the user through the medium of the displaying unit 24 by displaying the result as "bind" on the screen. Moreover, additional information such as nucleotide sequence or the length of the sequence is also provided to the user by displaying them on the screen. The determination result provided to the user may be output in the form of a hard copy from a printer, or it may be stored in a storage medium such as a floppy (registered trade mark) disk, hard disk, CD-ROM, DVD or flash memory.

Figure 14:
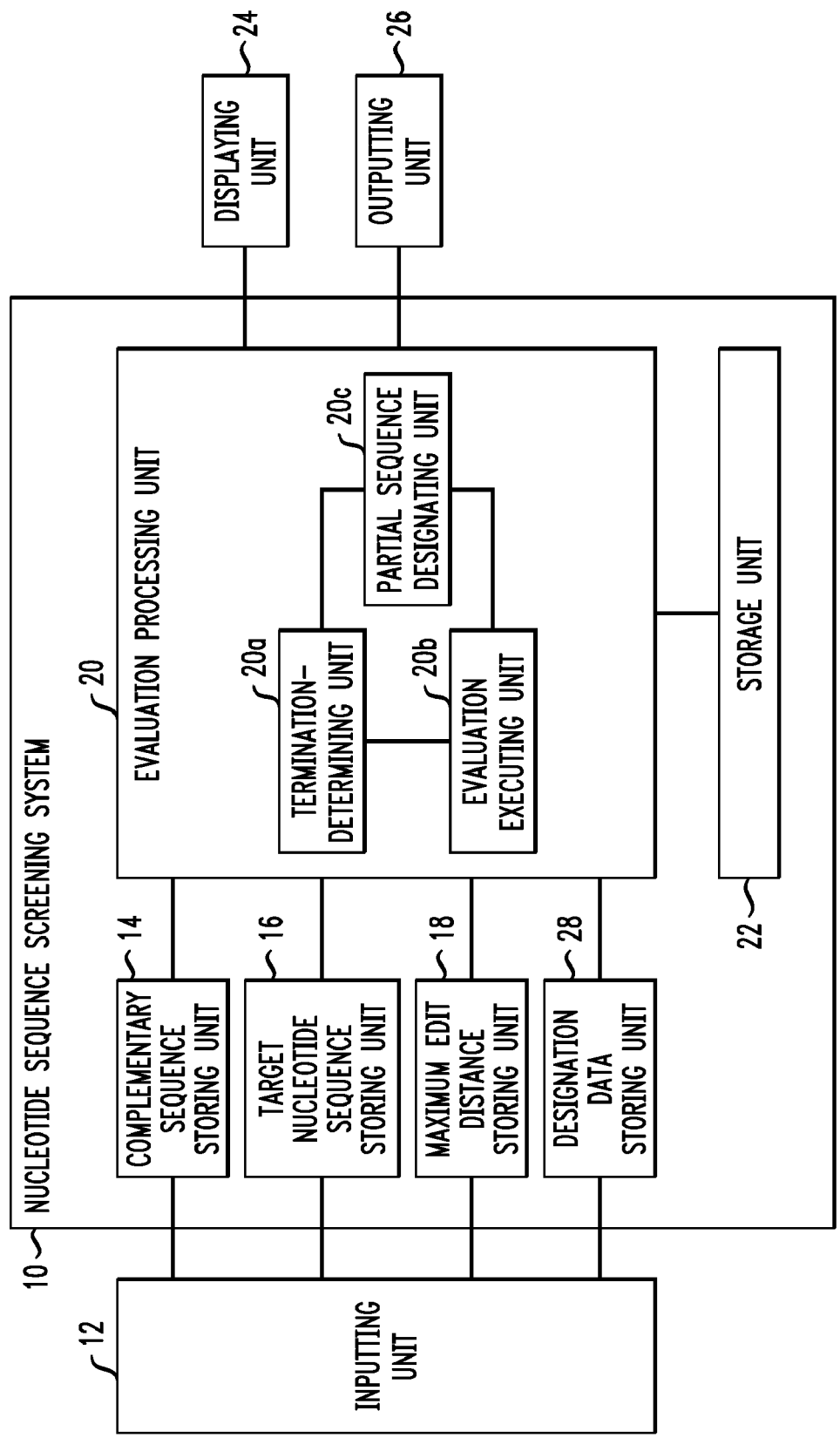
FIG. 14 is a view showing the second embodiment of the nucleotide sequence screening system of the present invention.

FIG. 14 is a view showing an embodiment of a system for implementing the second embodiment of the screening method of the present invention. The system 10 shown in FIG. 14 has almost the same configuration as that described in FIG. 13 except for the configuration of the evaluation processing unit 20. Accordingly, an evaluation processing unit 20 in the system 10 shown in FIG. 14 will be described in detail below. The evaluation processing unit 20 shown in FIG. 14 comprises a termination-determining unit 20a, an evaluation executing unit 20b, and a partial sequence designating unit 20c. The partial sequence designating unit 20c reads out information regarding a partial sequence to be initially evaluated, such as the value of position and the value of length, from a designation data storing unit 28, and determines the partial sequence to be evaluated. The designated partial sequence is passed to the evaluation executing unit 20b, and evaluation is carried out therein in the same manner as described in FIG. 13. The termination-determining unit 20a commands termination of the evaluation to the evaluation executing unit 20b as well as commanding termination of the evaluation of the partial sequence also to the partial sequence designating unit 20c. Moreover, when another partial sequence should be evaluated, a partial sequence to be evaluated next is designated, and the data of the partial sequence is transferred to the evaluation executing unit 20b.

Figure 15:
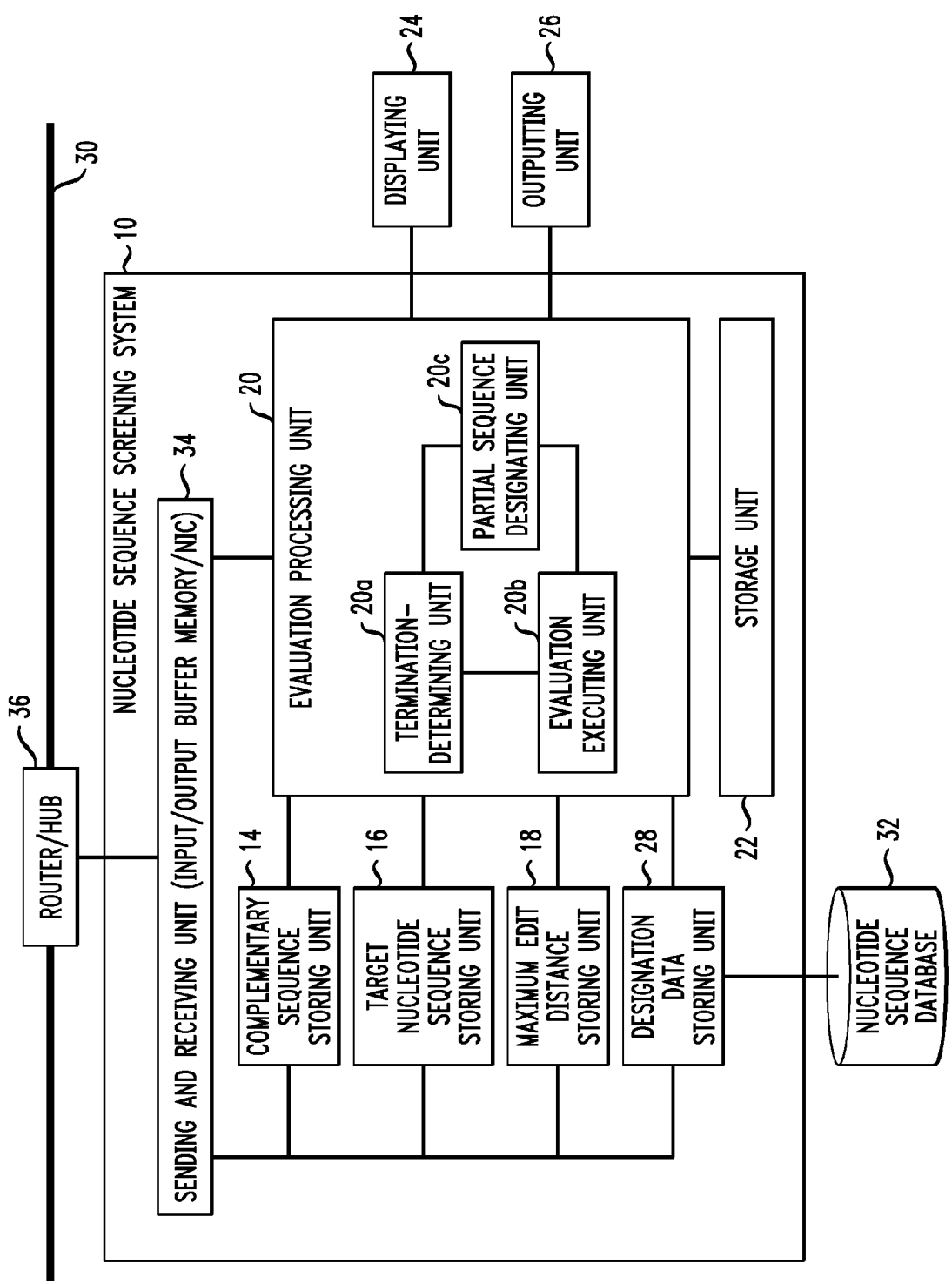
FIG. 15 is a view showing the third embodiment of the nucleotide sequence screening system of the present invention.

FIG. 15 is a view showing the second embodiment of the system 10 of the present invention. The system of the second embodiment of the present invention, as shown in FIG. 14, receives the data of a target nucleotide sequence T and the nucleotide sequence of a probe P from the user through a network 30. The received data is stored in the input buffer of a sending and receiving unit 34, and then stored in the complementary sequence storing unit 14, the target nucleotide sequence storing unit 16, the maximum edit distance storing unit 18, and the designation data storing unit 28. In this case, the user can directly send the target nucleotide sequence T. However, when the system 10 comprises a database for storing information regarding the target nucleotide sequence T, such as a cDNA database, the evaluation processing unit 20 refers to target designation data received from the user through the network, accesses to a database 32 to obtain the corresponding target nucleotide sequence, and stores the obtained target nucleotide sequence T in the target nucleotide sequence storing unit 16. The evaluation processing unit 20 carries out the same step as explained in FIG. 14 so as to generate an evaluation result, stores the evaluation result in a storage unit 22, as well as sending the result to a sending and receiving unit 34. Then, the evaluation result is sent out to the user through the network 30, so that information regarding the usefulness of the probe P for screening nucleotide sequences, which is stored in a nucleotide sequence database, is returned to the user.

EXAMPLES

In order to verify the effect of the screening method of the present invention, the program of the present invention was installed in a personal computer equipped with Windows® 2000 (with installation of Pentium® 4:2.2 GHz processor manufactured by Intel), and the calculation of the present method was analyzed by comparing with the conventional high-precision method (Smith-Waterman method). The genome of *Escherichia coli* with a nucleotide chain length of 4,639,221 bp that was acquired from a library (Gen Bank Accession No: NC_000913) was used as a target nucleotide sequence. An algorithm with the pseudo-codes shown in FIGS. 9 and 10 executing evaluation on the basis of every partial sequence, was installed in the personal computer used for this experiment. In addition, the Smith-Waterman method was applied as a function of check_exactly.

As a complementary sequence Q to be input, a nucleotide chain having a nucleotide chain length of approximately 580 bp was prepared by using a portion of the above genome of *Escherichia coli* and deleting several nucleotides therefrom, so as to prepare multiple probes P. The smallest window size (check_length) was fixed at 1158 that corresponds to about twice as long as the length of a probe. The edit distance k was set such that the similarity of a nucleotide chain capable of hybridization was set to 0.80, 0.85, 0.90, and 0.95. Thus, the experiment was carried out 4 times in which the similarity of the complementary sequence is different. Moreover, to make comparison, the calculation time obtained by the Smith-Waterman method as a prior art technique was also measured. The results are shown in FIG. 16.

From the results shown in FIG. 16, it was confirmed that the screening of the present invention was approximately twice to twenty times as fast as the conventional method in terms of calculation speed. With regard to the calculation speed, if the similarity can be set at high, the maximum edit distance k can be set at short, and accordingly, the repetitive calculation regarding the nucleotide sequence of the probe P can be limited (i.e., the repetition number of the edit distance counter can be k or less). Thus, the absolute number of nucleotides to be determined is decreased, thereby enabling high-speed calculation. That is to say, the present invention differs from the conventional method, and it enables high-precision calculation, as similarity is set at high.

The results shown in the table in FIG. 16 are plotted as a graph shown in FIG. 17 in which the vertical column represents calculation time (s) and the horizontal column represents similarity (%). FIG. 17 shows that, as similarity increases, the time to obtain a determination result is reduced. Moreover, it was also shown that when similarity is 100%, the time required to obtain a determination result is at least several ten times faster than the time required in the Smith-Waterman method as a comparative example.

Specific embodiments of the prevent invention have been described as above with reference to the drawings. Means or parts realizing the above described functions of the present invention can be configured as software or a group of software modules described in a computer executable programming language, and so they are not necessarily be function blocks described in the drawings. Moreover, in the nucleotide sequence screening system of the present invention, each function element can be configured with any function module, as necessary, and so it is not limited to specific embodiments shown in the drawings.

Furthermore, the program of the present invention can be written in various types of programming languages such as, by way of example only, FORTRAN, C language, C++ language, or JAVA®. Code including the program of the present invention may be retained in a computer-readable recording medium such as a magnetic tape, flexible disk, hard disk, compact disk (CD), magneto-optical disk, or digital versatile disk (DVD). It may also be distributed as a transmission medium.

By selectively eliminating at least probes with low complementarity, the present invention provides the user with good information regarding probes at a high speed, rather than the conventional method of using a high-precision alignment. Moreover, by applying the method of the present invention to the first screening for a probe and, after the screening, using the present method in combination with the convention method of using a high-precision alignment, the present invention also provides: a nucleotide sequence screening system capable of screening for a probe with a higher speed; a method therefor; a program causing a computer to execute the method; a computer-readable recording medium for storing the program; and a server on which the screening of nucleotide sequences is executed through the network.

Although illustrative embodiments of the present invention have been described herein with reference to the accompanying drawings, it is to be understood that the invention is not limited to those precise embodiments, and that various other changes and modifications may be affected therein by one skilled in the art without departing from the scope or spirit of the invention.

What is claimed is:

1. A computer system for screening nucleotide sequences, wherein the system comprises one or more distinct units, each of the one or more distinct units being embodied on a tangible computer-readable recordable storage medium, and wherein the system comprises:

a target nucleotide sequence storing unit for storing target nucleotide sequence data, wherein the target nucleotide sequence data is obtained from a target nucleotide sequence, and wherein the target nucleotide sequence storing unit executes on a hardware processor;

a complementary sequence data storing unit for generating complementary sequence data of a probe from a probe nucleotide sequence, wherein the probe nucleotide sequence may be bound to the target nucleotide sequence, and storing the complementary sequence data, wherein the complementary sequence data storing unit executes on a hardware processor;

an evaluation processing unit for designating one or more partial short chain sequences from said target nucleotide sequence data, as well as evaluating said complementary sequence data on the basis of each of the one or more partial sequences in descending order from a first edit distance value to a second edit distance value, the second edit distance value being lower than the first edit distance value, and determining the binding possibility of said probe nucleotide sequence to said target nucleotide sequence on a basis of the one or more partial sequences, and wherein the evaluation processing unit executes on a hardware processor;

a maximum edit distance storing unit for storing a maximum acceptable edit distance between said target nucleotide sequence and said probe nucleotide sequence, wherein the maximum edit distance storing unit executes on a hardware processor;

a termination-determining unit for dynamically determining termination of the evaluation, wherein the termination-determining unit executes on a hardware processor and wherein the termination-determining unit compares a value of min_k and the maximum edit distance k, wherein min_k represents a minimum value of edit distance, and wherein the termination-determining unit commands the evaluation processing unit to stop evaluating at a point when the value of min_k becomes greater than k; and a storage unit for storing a result from the evaluating step and the determining step obtained by said evaluation processing unit, wherein the storage unit executes on a hardware processor.

2. The computer system according to claim 1, wherein said termination-determining unit determines whether the evaluation of said complementary sequence data is carried out over said maximum edit distance.

3. The computer system according to claim 2, wherein said evaluation processing unit, in response to the determination by said unit for dynamically determining termination of the evaluation, causes said partial sequence designating unit to designate another partial sequence having a predetermined overlap with the partial sequence most recently evaluated.

4. A method for controlling a computer, which causes a computer system to execute screening of nucleotide sequences, wherein the method is run on a system comprising one or more distinct units, each of the one or more distinct units being embodied on a tangible computer-readable recordable storage medium, and wherein the method causes the computer system to execute:

a step of storing target nucleotide sequence data and a probe nucleotide sequence, wherein the target nucleotide sequence data is obtained from a target nucleotide sequence, and wherein storing target nucleotide sequence data is carried out by a target nucleotide sequence storing unit executing on a hardware processor;

a step of generating complementary sequence data of a probe from a probe nucleotide sequence, wherein the probe nucleotide sequence may be bound to the target nucleotide sequence, and storing the complementary sequence data, wherein generating complementary sequence data is carried out by a complementary sequence data storing unit executing on a hardware processor;

a step of storing a maximum edit distance between said target nucleotide sequence and said probe nucleotide sequence, wherein storing the maximum edit distance is carried out by a maximum edit distance storing unit executing on a hardware processor;

a step of designating one or more partial short chain sequences from said target nucleotide sequence data, as well as evaluating said complementary sequence data on the basis of each of the one or more partial sequences in descending order from a first edit distance value to a second edit distance value, the second edit distance value being lower than the first edit distance value, and determining the binding possibility of said probe nucleotide sequence to said target nucleotide sequence on a basis of the one or more partial sequences, wherein the designating, evaluating and determining steps are carried out by an evaluation processing unit executing on a hardware processor;

a step of dynamically determining termination of the evaluation, wherein dynamically determining termination of the evaluation is carried out by a termination-determining unit executing on a hardware processor, and wherein the termination-determining unit compares a value of min_k and the maximum edit distance k, wherein min_k represents a minimum value of edit distance, and wherein the termination-determining unit commands the evaluation processing unit to stop evaluating at a point when the value of min_k becomes greater than k; and a step of storing a result from said evaluation steps in a storage unit, wherein storing the result of the evaluation steps is carried out by a storage unit executing on a hardware processor.

5. The method for controlling a computer according to claim 4, wherein said evaluating step further comprises:

a step of determining whether the evaluation of said complementary sequence data is earned out over said maximum edit distance regarding at least one of said partial sequences; and a step of dynamically terminating the evaluation in response to said determination result.

6. The method for controlling a computer according to claim 5, wherein said evaluating step further comprises:

a step of determining termination of the evaluation; and a step of designating another partial sequence having a predetermined overlap with the partial sequence most recently evaluated, in response to the determination of said termination of the evaluation.

7. A method for making a computer implemented process to enable screening of nucleotide sequences, wherein the method is run on a system comprising one or more distinct units, each of the one or more distinct units being embodied on a tangible computer-readable recordable storage medium, the method comprising the steps of:

instantiating first computer instructions onto a computer readable medium, the first computer instructions configured to store target nucleotide sequence data and a probe nucleotide sequence, wherein the target nucleotide sequence data is obtained from a target nucleotide sequence, and wherein storing target nucleotide sequence data is carried out by a target nucleotide sequence storing unit executing on a hardware processor;

instantiating second computer instructions onto a computer readable medium, the second computer instructions configured to generate complementary sequence data of a probe from a probe nucleotide sequence, wherein the probe nucleotide sequence may be bound to the target nucleotide sequence, and storing the complementary sequence data, wherein generating complementary sequence data is carried out by a complementary sequence data storing unit executing on a hardware processor;

instantiating third computer instructions onto a computer readable medium, the third computer instructions configured to store a maximum edit distance between said target nucleotide sequence and said probe nucleotide sequence, wherein storing the maximum edit distance is carried out by a maximum edit distance storing unit executing on a hardware processor;

instantiating fourth computer instructions onto a computer readable medium, the fourth computer instructions configured to designate one or more partial short chain sequences from said target nucleotide sequence data, as well as evaluating said complementary sequence data on the basis of each of the one or more partial sequences in descending order from a first edit distance value to a second edit distance value, the second edit distance value being lower than the first edit distance value, and determining the binding possibility of said probe nucleotide sequence to said target nucleotide sequence on a basis of the one or more partial sequences, wherein the designating, evaluating and determining steps are carried out by an evaluation processing unit executing on a hardware processor;

instantiating fifth computer instructions onto a computer readable medium, the fifth computer instructions configured to dynamically determine termination of the evaluation, wherein dynamically determining termination of the evaluation is carried out by a termination-determining unit executing on a hardware processor, and wherein the termination-determining unit compares a value of min_k and the maximum edit distance k, wherein min_k represents a minimum value of edit distance, and wherein the termination-determining unit commands the evaluation processing unit to stop evaluating at a point when the value of min_k becomes greater than k; and instantiating sixth computer instructions onto a computer readable medium, the sixth computer instructions configured to store a result from said evaluation steps in a storage unit, wherein storing the result of the evaluation steps is carried out by a storage unit executing on a hardware processor.

8. The method of claim 7, wherein the step of instantiating fourth computer instructions further comprises:

instantiating seventh computer instructions onto a computer readable medium, the seventh computer instructions configured to determine whether the evaluation of said complementary sequence data is carried out over said maximum edit distance regarding at least one of said partial sequences;

instantiating eighth computer instructions onto a computer readable medium, the eighth computer instructions configured to dynamically terminate the evaluation in response to said determination result; and instantiating ninth computer instructions onto a computer readable medium, the ninth computer instructions configured to designate another partial sequence having a predetermined overlap with the partial sequence most recently evaluated, in response to the determination of said termination of the evaluation.

9. A computer-readable storage medium for recording a computer executable program for a method for controlling a computer, which causes a computer system to execute screening of nucleotide sequences, said program controlling said computer system and causing the computer system to execute:

a step of storing target nucleotide sequence data and a probe nucleotide sequence, wherein the target nucleotide sequence data is obtained from a target nucleotide sequence;

a step of generating complementary sequence data of a probe from a probe nucleotide sequence, wherein the probe nucleotide sequence may be bound to the target nucleotide sequence and storing the complementary sequence data;

a step of storing a maximum edit distance between said target nucleotide sequence and said probe nucleotide sequence;

a step of designating one or more partial short chain sequences from said target nucleotide sequence data, as well as evaluating said complementary sequence data on the basis of each of the one or more partial sequences in descending order from a first edit distance value to a second edit distance value, the second edit distance value being lower than the first edit distance value, and evaluating the binding possibility of said probe nucleotide sequence to said target nucleotide sequence on a basis of the one or more partial sequences;

a step of dynamically determining termination of the evaluation, wherein dynamically determining termination of the evaluation comprises comparing a value of min_k and the maximum edit distance k, wherein min_k represents a minimum value of edit distance, and stopping the evaluation at a point when the value of min_k becomes greater than k; and a step of storing a result of said evaluation steps in a storage unit.

* * * * *

SEQUENCE LISTING

<160> NUMBER OF SEQ ID NOS: 6

<210> SEQ ID NO 1
<211> LENGTH: 10
<212> TYPE: DNA
<213> ORGANISM: Artificial
<220> FEATURE:
<223> OTHER INFORMATION: Synthetic

```
<400> SEQUENCE: 1
atggcctgac                                                              10

<210> SEQ ID NO 2
<211> LENGTH: 10
<212> TYPE: DNA
<213> ORGANISM: Artificial
<220> FEATURE:
<223> OTHER INFORMATION: Synthetic

<400> SEQUENCE: 2
gtcaggccat                                                              10

<210> SEQ ID NO 3
<211> LENGTH: 13
<212> TYPE: DNA
<213> ORGANISM: Artificial
<220> FEATURE:
<223> OTHER INFORMATION: Synthetic

<400> SEQUENCE: 3
gtagtcaggc cat                                                          13

<210> SEQ ID NO 4
<211> LENGTH: 12
<212> TYPE: DNA
<213> ORGANISM: Artificial
<220> FEATURE:
<223> OTHER INFORMATION: Synthetic

<400> SEQUENCE: 4
atgcgcgtaa gt                                                           12

<210> SEQ ID NO 5
<211> LENGTH: 11
<212> TYPE: DNA
<213> ORGANISM: Artificial
<220> FEATURE:
<223> OTHER INFORMATION: Synthetic

<400> SEQUENCE: 5
atgcgttaac t                                                            11

<210> SEQ ID NO 6
<211> LENGTH: 10
<212> TYPE: DNA
<213> ORGANISM: Artificial
<220> FEATURE:
<223> OTHER INFORMATION: Synthetic

<400> SEQUENCE: 6
cgcgcatgaa                                                              10
```